United States Patent [19]

Högberg et al.

[11] 4,049,800

[45] Sept. 20, 1977

[54] METHOD, COMPOSITION AND COMPOUNDS FOR TREATING EXCESS PROSTAGLANDINS

[75] Inventors: Bertil Högberg; Hans Fex; Torsten Perklev; Sten Veige, all of Helsingborg; Bo Fredholm, Nyhamnslage, all of Sweden

[73] Assignee: Aktiebolaget Leo, Helsingborg, Sweden

[21] Appl. No.: 716,197

[22] Filed: Aug. 20, 1976

Related U.S. Application Data

[62] Division of Ser. No. 519,542, Oct. 31, 1974, which is a division of Ser. No. 280,276, Aug. 14, 1972, Pat. No. 3,851,019.

[30] Foreign Application Priority Data

| Aug. 17, 1971 | United Kingdom | 38579/71 |
| Aug. 17, 1971 | United Kingdom | 38580/71 |
| Jan. 31, 1972 | United Kingdom | 4508/72 |
| Jan. 31, 1972 | United Kingdom | 4509/72 |

[51] Int. Cl.$^2$ .................. C07F 9/09; A01N 9/36
[52] U.S. Cl. ..................................... 424/211
[58] Field of Search .............. 260/943, 944; 424/211

[56] References Cited

U.S. PATENT DOCUMENTS 2,915,547  12/1959  Atherton ........................ 260/943

Primary Examiner—Anton H. Sutto
Attorney, Agent, or Firm—Gordon W. Hueschen

[57] ABSTRACT

This invention relates to novel secondary phosphoric acid esters and salts thereof, having valuable pharmacological properties, and to the preparation thereof. The invention is also concerned with pharmaceutical compositions containing the said compounds, and methods of treatment therewith.

The esters are i.a. useful as selective inhibitors of prostaglandins and of Slow Reacting Substances (SRS). They also inhibit the formation of adenosine 3',5'-monophosphate (cyclic AMP).

In addition the esters of this invention also exert intrinsic smooth muscle stimulatory activity.

16 Claims, No Drawings

METHOD, COMPOSITION AND COMPOUNDS FOR TREATING EXCESS PROSTAGLANDINS

The application is a division of application Ser. No. 519,542, filed Oct. 31, 1974, which is in turn a division of application Ser. No. 280,276, filed Aug. 14, 1972, now issued U.S. Pat. No. 3,851,019.

The present invention relates to novel secondary phosphoric acid esters and salts thereof, having valuable pharmacological properties, as well as processes for the preparation thereof. The invention is also concerned with pharmaceutical compositions containing the said compounds, and methods of treatment therewith.

The compounds have all strong activity as selective inhibitiors of prostaglandins or of compounds with structures related to the naturally occuring prostaglandins and having the same type of activities as those. They also selectively antagonize the Slow Reacting Substance (SRS), an unsaturated hydroxy-acid of lipid nature related to the prostaglandins and inhibit the formation of adenosine 3',5'-monophosphate (cyclic AMP), a key component of the cellular response to extracellular events, which is interrelated to the action of prostaglandin.

Like many substances with receptor blocking properties, e.g. certain adrenergic $\beta$-blocking agents, the compounds of this invention also exort intrinsic in this case smooth muscle stimulatory activity.

These esters are also useful as surface active agents and as agents in extractions of cations due to the presence of both hydrophilic and lipophilic groups of the same molecule. They also exert corrosion-inhibitory effects.

BACKGROUND OF THE INVENTION

The prostaglandins (in the following abbreviated as PG:s) are a new group of biologically active substances affecting many important physiological processes largely by influencing intracellular metabolism. See e.g. E. W. Horton in "Prostaglandins" (Monographs, Endocrinology, Vol. 7, 1972; Springer-Verlag).

The basic chemical structure of the PG:s is a $C_{20}$ fatty acid, prostanoic acid, containing a five-membered ring.

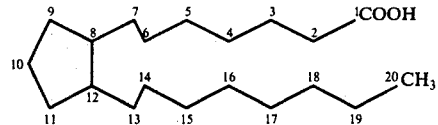

Depending on the substituents in the five-membered ring four different abbreviations are used in the literature.

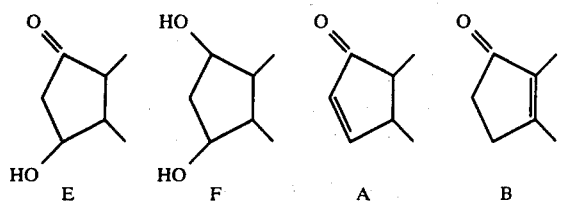

All E-types PG:s have 11$\alpha$-hydroxy and 9-keto groups in the cyclopentane ring. In the F-types the 9-keto group is reduced to a ($\alpha$ or $\beta$) hydroxyl group. All the "primary$\rightleftharpoons$ PG:s contain a 13:14 trans double bond. $E_1$ and $F_1$ compounds have only this one double bond the $E_2$ and $F_2$ molecules have an additional 5:6 cis double bond and the $E_3$ and $F_3$ a further cis double bond between 17 and 18. All naturally occuring PG:s found today have a 15(S)-hydroxy group. 9$\alpha$,11$\alpha$,15(S)-tri hydroxy-5-cis, 13-transprostadienoic acid has for example, been called prostaglandin $F_{2\alpha}$ and further abbreviated as $PGF_{2\alpha}$.

Details about the chemistry of the PG:s are found, e.g. in a review by P. W. Ramwell et al, in "Progress in the chemistry of fats and other lipids" vol. IX, p. 231.

It is also known that compounds with a structure related to the naturally occuring PG:s can have similar effects. See e.g. P. W. Ramwell et al., Nature 221 (1969) 1251, W. Lippman, J. Pharm. Pharmacol. 22 (1970) 65, J. Fried et al., J. Am. Chem. Soc. 97 (1971) 7319 and N. S. Crossley, Tetrahedron Letters (1971), 3327.

Evidence that PG:s are involved in a large number of physiological and pathological processes is rapidly accumulating. Two major areas, where these compounds play an important physiological role, are the control of fertility and the regulation of blood flow. Further, the PG:s have potent pharmacological actions on smooth muscle in various other organs such as the gastrointestinal and the respiratory tracts. They are also involved in the events following nerve stimulation, both centrally and in the periphery, as well as in the process of lipolysis. There are also indications that PG:s play an important role in different ophthalmologic disorders.

In the area of reproduction PG:s are involved in several ways. It is known, for instance, that sufficient amounts of PG:s to affect the female genital-tract smooth muscles are delivered with the semen and thereby probably promote conception. At full term the levels of PG:s in plasma and amniotic fluid are increased which in turn initiates the onset of labour. This latter effect of PG:s is presently being used therapeutically.

The circulatory effects of PG:s are as a rule vasodepressive, although PGF in some instances may cause a rise of the blood-pressure. The way in which PG:s normally contribute to bloodflow regulation has not yet been elucidated.

In the gastrointestinal tract PG:s generally cause contraction of the smooth muscle. Certain kinds of diarrhoea are believed to be caused by high plasma levels of PG:s. In the lungs PGF causes bronchonstriction, while PGE has the opposite effect. At nerve stimulation PG:s are released and, at least in peripheral nerves, seem to counteract the result of the stimulation.

The effects of PG:s are generally obtained with very small amounts of the compounds, and this observation, together with the fact that PG:s are widely distributed in the organism point to an important role of these compounds in homeostatic mechanisms. However, although so many important pharmacological effects of PG:s are known, the exact nature of their physiological involvements is poorly understood. There is in part due to the fact that no suitable inhibitory compound has so far been available.

Having very pronounced physiological and pharmacological effects the PG:s could safely be anticipated also to play an important role in pathological conditions. Accordingly, there is now rapidly growing evidence for this, a fact that further emphasizes the need for prostaglandin-inhibitory agents. Thus, PG:s are involved in inflammatory processes of various kinds, such as burns, contact dermatitis and anaphylactic reactions. In these cases PG:s have been suggested to be mediators of the reaction. One important condition, for example, in which PG:s are considered to be of etiological significance, is bronchial asthma. In this connection it is of interest to mention that a substance, chemically and pharmacologically closely related to the prostaglandins, namely Slow Reacting Substance (SRS, Cf. Strandberg, K. and Uvnas, B. in Acta Physiol. Scand. 82 (1971) p. 358), is also produced during anaphylaxis, e.g. in bonchial asthma. A possibility to counteract the effect of this substance is thus also highly desirable.

Against the background of the above information it is evident that major therapeutic advances may result from the use of prostaglandin-inhibitory substances. Inhibition of various inflammatory reactions, improvement of bronchial asthma, regulation of bloodflow, control of gastroinstestinal hypermotility are a few examples of expected therapeutic effects of such compounds. With increasing knowledge about the functions of PG:s the usefulness of inhibitors therefore will no doubt become still more apparent. Not only will conditions characterized by an excessive formation of PG:s by improved, but it is also possible to influence certain normal physiological processes when so desired, such as for example the conception.

Therapeutic advances may further result from administering esters of this invention before, at the same time or after the administration of PG:s in order to prevent side-effects caused by the PG:s, e.g. diarrhoea, nausea, vomiting, local tissue reactions and pyrexia.

The expression "prostaglandins" (PG:s) are used in this disclosure is intended to cover prostaglandins and related structures as indicated above of natural as well as synthetic orgin.

In addition the esters of this invention exert an inhibitory action on the hormone stimulated formation of adenosine 3',5'-monophosphate (cyclic AMP). Cyclic AMP is formed from adenosine 5'-triphosphoric acid (ATP) by the action of adenyl cyclase, an enzyme system contained in the plasma membrane. The hormones influence this enzyme complex and thereby the intracellular concentration of cyclic AMP. The cells respond to the changes in cyclic AMP levels with whatever mechanism the different cells have available. It seems likely that compounds which influence the formation of cyclic AMP will be of therapeutic value, when increasing knowledge about the cellular dysfunction at different pathological conditions will ba available. See e.g. G. A. Robinson et al. in "Cyclic AMP", Academic Press 1971.

Some antagonists of prostaglandins have already been described. J. Fried et al., Nature 223 (1969) 208, found that 7-oxa-prostaglandin-like compounds with 6-membered rings inhibited prostaglandin $E_1$ ($PGE_1$).

A derivative of dibenzoxazepine was found to antagonize $PGE_2$ (J. H. Sanner in Arch. int. Pharmacodyn. 180 (1969) 46.)

A high molecular weight polyester between phloretin and phosphoric acid was also found to have a prostaglandin-blocking activity (K. E. Eakins et al. Brit. J. Pharmac. 39 (1970) 556), and in addition to be an antagonist of Slow Reacting Substance (SRS) (Mathe, A.A., and Strandberg K. in Acta physiol. scand. 82 (1971) 460).

This polymer, polyphoretin phosphate, was already described by E. Diszfalusy et al. in Acta Chem. Scand. 7 (1953) 913, as a cross-linked high molecular weight enzyme inhibitor. It has an average molecular weight of 15,000, did not dialyze through a cellophane membrane, and was found to be a strong inhibitor of various enzymes e.g. hyaluronidase and alkaline phosphatase.

These materials are complex mixtures of various different polymeric structures in varying proportions (due to the inability to control either the degree of polymerisation or selectively induce such polymerisation at specific reactions sites in view of the availability of numerous possible sites at which polymerisation can occur) and the activity which has been attributed thereto could not be attributed to any specific polymeric structure, much less any specific molecular weight fraction of any certain structures or units thereof, either in theory or in practice, in which latter aspect positive identification of specific active components of the complex polymeric mixture has been impossible.

It has now, surprisingly, been found that certain simple synthetic seconary phosphoric acid esters of the structures shown below are very good selective inhibitors of PG:s and compounds with prostaglandin activities and that they also selectively antagonize the Slow Reacting Substance (SRS). These effects are shown in examples Nos. 21-25.

From the results obtained in those examples it is obvious that the compounds of this invention are useful when it is desired to inhibit the effects caused by various PG:s and also of the effect of SRS.

Example No 26 shows that the compounds also can prevent or reduce an anaphylactic bronchoconstriction.

The inhibitory effect of esters of this invention on the formation of cyclic AMP is described in example No. 27.

This example shows the usefulness of the compounds to prevent the formation of cyclic AMP and thus improve a condition where an excessive formation of that compound occurs. 28-30.

In addition the esters of this invention exert a smooth muscle stimulatory activity as demonstrated in examples Nos.

Since the compounds of the invention are produced synthetically, they have a definitive structure and are of course substantially free or inactive or lesser active impurities and materials of similar and/or indefinite composition and a structure.

In the types of experiments described by Eakins et al. (ibid.) and by Perklev & Ahren (Life Sciences Part I, 10 (1971) 1387)most of the compounds of this invention are much stronger inhibitors against prostaglandins, e.g. $E_1$ ($PGE_1$), $E_2$ ($PGE_2$), $F_{1\alpha}$ ($PGF_{1\alpha}$) and $F_{2\alpha}$ ($PGF_{2\alpha}$) than polyphloretin phosphate and they are also superior as antagonists for Slow Reacting Substance (SRS) in the types of experiments described by Mathe and Strandberg (ibid.). In addition the secondary phosphoric acid esters of this invention have no such antienzymatic properties as those described for this cross-linked high molecular weight polymer.

SUMMARY OF THE INVENTION

Accordingly, one object of the invention is to provide new compounds possessing activity as selective inhibitors of prostaglandins and compounds with prostaglandin activities.

Another object of the invention is to provide new compounds possessing activity as selective inhibitors of the Slow Reacting Substances (SRS).

A further object of the invention is to provide new compounds possessing activity as inhibitors of the formation of adenosine 3',5'-monophosphate (cyclic AMP).

Still another object of the invention is to provide new compounds having a smooth muscle stimulatory effect.

Another object of the invention is to provide processes for preparing the new compounds.

A further object of the invention is to provide a method of treating a living animal body to produce a prostaglandin inhibitory effect.

Yet another object of the invention is to provide a method of treating a living animal body to produce an antagonizing effect of the Slow Reacting Substance (SRS).

Still another object of the invention is to provide a method of treating a living animal body to produce an inhibition of the formation of adenosine 3',5'-monophosphate (cyclic AMP).

Yet another obect of the invention is to provide a method of treating a living animal body to produce a smooth muscle stimulatory effect.

A further object of the invention is to provide compositions containing as an active ingredient one or more of the new compounds preferably together with a pharmaceutically acceptable carrier and, if desired, other pharmacologically active agents.

According to the invention there are provided novel compounds having the general formula $$A-O-\underset{\underset{OM}{|}}{\overset{\overset{O}{\|}}{P}}-O-B \qquad (I)$$

wherein M is selected from the group consisting of hydrogen; and a pharmaceutically acceptable inorganic and organic cations; and wherein A is:

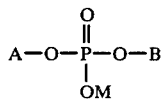

wherein one and only one of the substituents $R^6$, $R^7$, and $R^{13}$ always represents a group R, located in any of the ortho, meta and para positions relative to the phosphoric acid ester group, the group R having the formula:

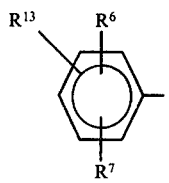

wherein X is selected from the group consisting of:

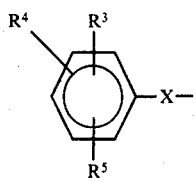

wherein $q$ is selected from the group consisting of zero and one; and wherein Z is selected from the group consisting of:

straight saturated hydrocarbon chains having at most 3 carbon atoms; and straight hydrocarbon chains having 2 and 3 carbon atoms and containing one double bond.

The ketogroup of X may also be in the form of a ketal of a lower aliphatic alcohol;

wherein Z above may be substituted by one substituent selected from the group consisting of:

lower alkyl; lower alkenyl; lower alkoxy; hydroxy; —O—CO—$R^{14}$; cyclopentyl; cyclohexyl; phenyl; phenyl substituted in m- or p-position by one substituent selected from the group consisting of lower alkyl, lower alkoxy, —F—, —Cl, —Br, and —CF$_3$; benzyl; benzyl substituted in m- or p-position by one substituent selected from the group consisting of lower alkyl, lower alkoxy, —F, —Cl, —Br, and —CF$_3$; benzylidene; benzylidene substituted in m- or p-position by one substituent selected from the group consisting of lower alkyl, lower alkoxy, —F, —Cl, —Br, and —CF$_3$; with the proviso that not more than one substituent selected from the group consisting of: lower alkoxy; hydroxy; and —O—CO—$R^{14}$ is present in Z; and that not more than one substitutent selected from the group consisting of: cyclopentyl; cyclohexyl; phenyl; substituted phenyl; benzyl; substituted benzyl; benzylidene; and substituted benzylidene is present in Z; wherein B in the general formula (I) above is selected from the group consisting of:

alkyl, having 1 to 8 carbon atoms, inclusive, optionally mono- and di-substituted; cycloakyl, namely cyclopentyl and cyclohexyl, optionally mono- and di-substituted; 1-naphthyl and 2-naphthyl, both naphthyls being optionally mono- and di-substituted; 2-, 3- and 4-biphenylyl, any biphenylyl being optionally mono- and di-substituted; and

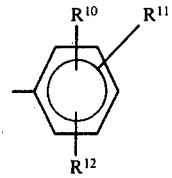

wherein $R^3$, $R^4$, $R^5$, $R^6$, $R^7$, $R^{10}$, $R^{11}$, $R^{12}$ and $R^{13}$ above are selected from the group consisting of:

hydrogen; lower alkyl; lower alkenyl; lower alkoxy; hydroxy; —O—CO—$R^{14}$;

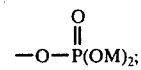

—F; —Cl; —Br; —CF$_3$; —CN; —NO$_2$; —COOR$^9$; —CH$_2$COOR$^9$; —OCH$_2$COOR$^9$; —CO—R$^{14}$; —CONR$_2^8$; —CH$_2$CONR$_2^8$; —OCH$_2$CONR$_2^8$; —NR$_2^8$; —NR$^8$—CO—R$^{14}$; —CH$_2$NR$_2^8$; and —CH$_2$NR$^8$—CO—R$^{14}$;

with the proviso that always one and only one of the substituents $R^6$, $R^7$, and $R^{13}$ is R;

wherein $R^8$ is selected from the group consisting of hydrogen and lower alkyl;

wherein $R^9$ is selected from the group consisting of lower alkyl and M, where M have the above meaning; and wherein $R^{14}$ is lower alkyl.

In this disclosure the optional substituents referred to above involve substituents selected from the group consisting of:

lower alkyl; lower alkoxy; —F; —Cl;—Br; and —CF₃;

As used herein, the structural presentation of a substituted benzene nucleus as per the basic formula:

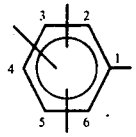

is intended to cover all possible variants with regard to the positions of the three nonfixed substituents, i.e. 2,3,4-, 2,3,5-, 2,3,6-, 2,4,5-, 2,4,6-, and 3,4,5-subtitution.

In this disclosure the expression "lower" means that the group referred to contains one to four carbon atoms, inclusive. Thus, lower alkyl, lower alkenyl and lower alkoxy include for instance: methyl, ethyl, propyl, isopropyl, butyl, secondary butyl, iso-butyl, tertiary butyl, vinyl, iso-propenyl, 1-propenyl, allyl, methoxy, ethoxy, propoxy, iso-propoxy, butoxy, iso-butoxy, secondary butoxy and tertiary butoxy.

Among pharmaceutically acceptable inorganic and organic cations under the definition of M above, those derived from the following metals and amines may be mentioned;

metals: calcium, potassium, and sodium,
amines: monoethanolamine, diethanolamine, dimethylaminoethanol, N-methylglucamine, trishydroxymethylmethylamine morpholine, and the like.

Among the compounds covered by the above general formula (I) those are preferred wherein B is selected from the group consisting of: aryl, particularly phenyl; substituted aryl, particularly phenyl substituted as per the above definition; alkyl having at least four carbon atoms; and substituted alkyl having at least four carbon atoms.

With regard to substituents $R^3$, $R^4$, $R^5$, $R^6$, $R^7$, and $R^{13}$, it is prefered that at least one of said substituents is hydrogen.

With regard to substituents $R^{10}$, $R^{11}$, and $R^{12}$, it is preferred that at least one of said substituents is hydrogen.

It is also preferred that, in addition to the one being R, at least one of substituents $R^3$, $R^4$, $R^5$, $R^6$, $R^7$, $R^{10}$, $R^{11}$, $R^{12}$, and $R^{13}$ is different from hydrogen.

If substituents $R^3$, $R^4$, $R^5$, $R^6$, $R^7$, $R^{10}$, $R^{11}$, $R^{12}$, and $R^{13}$, except that one being R, are all hydrogen, it is preferred that q is one and that Z is a substituted straight hydrocarbon chain.

Concerning the substituent R, those compounds are preferred where R is positioned in one of the m- and p-positions relative to the secondary phosphoric acid ester group.

Preferred compounds are obtained if Z is selected from the group consisting of unsubstituted and substituted straight hydrocarbon chains having at most two carbon atoms.

When q is one, preferred compounds are obtained if Z carries a substituent selected from the group consisting of lower alkyl, lower alkenyl, phenyl, substituted phenyl, benzyl, substituted benzyl, benzylidene, and substituted benzylidene.

If selected from the group consisting of —COOR⁹, —CH₂COOR⁹, —OCH₂COOR⁹, —CONR₂⁸, —CH₂CONR₂⁸, —OCH₂CONR₂⁸, —NR₂⁸, —NR⁸—CO—R¹⁴, —CH₂NR₂⁸, and —CH₂NR⁸—CO—R¹⁴, preferably only one of substituents R3, R⁴, R⁵, R⁶, R⁷, R¹³, and only one of substituents R¹⁰, R¹¹, and R¹² constitutes a substituent from said group.

A group of preferred compounds are those wherein the substituents $R^3$, $R^4$, $R^5$, $R^6$, $R^7$, $R^{10}$, $R^{11}$, $R^{12}$, and $R^{13}$, except the one being R, are selected from the group consisting of hydrogen, lower alkyl, lower alkoxy, hydroxy, —O—CO—R¹⁴,

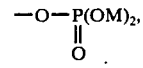

—F, —Cl, —Br, and —CF₃.

It is preferred that at most one of the substituents $R^3$, $R^4$, $R^5$, $R^6$, $R^7$, $R^{10}$, $R^{11}$, $R^{12}$, and $R^{13}$ consists of the group

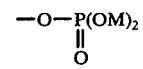

and that said group, which confers water solubility to the componds hereby obtained, preferably is positioned in one of the groups R and B, when B is a substituted phenyl group, and located in any of the m- and p-positions relative to X or relative to the secondary phosphoric acid ester group, respectively.

If selected from the group consisting of —F, —Cl, —Br, and —CF₃, preferably at most two of substituents $R^3$, $R^4$, $R^5$, $R^6$, $R^7$, $R^{10}$, $R^{11}$, $R^{12}$, and $R^{13}$ constitute a substituent from said group.

When q is one, preferred compounds are obtained if the carbonyl group of X is attached to the benzene nucleus of R.

Preferred compounds are also obtained when at least two of the substituents $R^3$, $R^4$, $R^5$, $R^6$, $R^7$, and $R^{13}$, except the one being R, are selected from the group consisting of lower alkyl, lower alkoxy, hydroxy, and —O—CO—R¹⁴. When B is a substituted phenyl group the substituents $R^{10}$, $R^{11}$, and $R^{12}$ are preferably selected from the group consisting of hydrogen, lowr alkyl, lower alkoxy, —F, —Cl, and —CF₃.

Another group of preferred compounds are those wherein at least two of the substituents $R^3$, $R^4$ and $R^5$ are selected from the group consisting of lower alkoxy, hydroxy, and —O—CO—R¹⁴, and the third substituent, if not selected from said group, is selected from the group consisting of hydrogen and lower alkyl; the substituents $R^6$, $R^7$, and $R^{13}$, except the one being R, selected from the group consisting of hydrogen, lower alkyl, and lower alkoxy; and wherein the group B is selected from the group consisting of alkyl having at least four carbon atoms, substituted alkyl having at least four carbon atoms, and

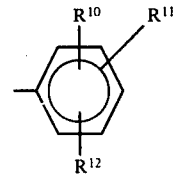

wherein $R^{10}$, $R^{11}$, and $R^{12}$ are selected from the group consisting of hydrogen, lower alkyl, lower alkoxy, —F, —Cl, and —CF₃

PREPARATION OF COMPOUNDS HAVING THE FORMULA (I) ABOVE.

The compounds having the above formula (I) may be prepared by methods known per se, see for instance Houben Weyl, Methoden der organischen Chemie, IV Ed. Vol. XII/2, p. 226. and the heading "Phosphorylation" by D. M. Brown, p. 75 in "Advances in Organic Chemistry", Vol. 3, Interscience Publishers, 1963.

Among such methods for instance the following are useful:

a. A primary phosphoric acid ester derived from a compound having formula (II) thus having the general formula (III)

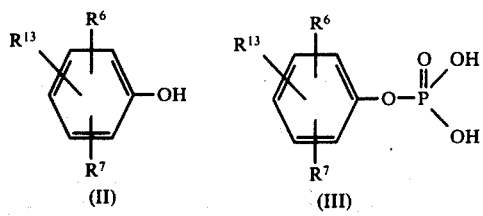

is allowed to react in an activated form with about 1 mole of a compound selected from aliphatic and cycloaliphatic alcohols, naphthols, biphenylols and

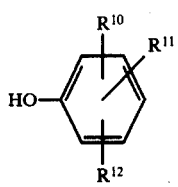

to form secondary phosphoric acid esters. This reaction may for instance be carried out in the presence of about 2 moles of 2,4,6-triisopropylbenzenesulphonyl chloride and about 2 moles of triethylamine using pyridine as a solvent. After the condensation has been completed the compounds are hydrolyzed with water making it possible to isolate the secondary phosphoric acid having the formula (I) above.

Methods for the preparation of the primary phosphoric acid esters having the formula (III) above are known per se, see for instance the first reference given above, p. 143, and the second one.

b. A compound of formula (II) above is treated with at least on mole of an aryl phosphorodichloridate having the formula

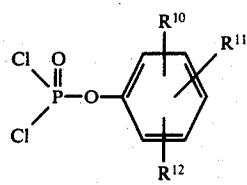

suitably in the presence of a tertiary amine, for instance dry pyridine. After the condensation unreacted chlorine atoms are hydrolyzed with water and the unsymmetrical secondary phosphoric acid ester obtained is isolated from the reaction mixture in the form of its free acid or as a suitable salt thereof.

Instead of the phosphorodichloridates having the formula (V) above also phosphorodichloridates from naphthols and biphenylols can be used.

Methods for the preparation of the aryl phosphorodichloridates mentioned above are known per se, see for instance the first reference given above (p. 212).

c. Compounds having the formula (I) above wherein B is an alkyl or a cycloalkyl group may also be prepared by starting with a primary phosphoric acid ester having formula (III) above, and activating such esters for instance by means of a carbodiimide or trichloro-acetonitrile and under such activated conditions reacting them with an aliphatic or cycloaliphatic alcohol to give the corresponding unsymmetrical secondary phosphoric acid esters.

d. The compounds according to the present invention wherein B is an alkyl or cycloalkyl group may also be prepared, by subjecting diphosphoric acid (pyrophosphate) triesters, having the formula (VI) below, to a solvolysis with the appropriate alcohol, for instance according to the reaction sequence:

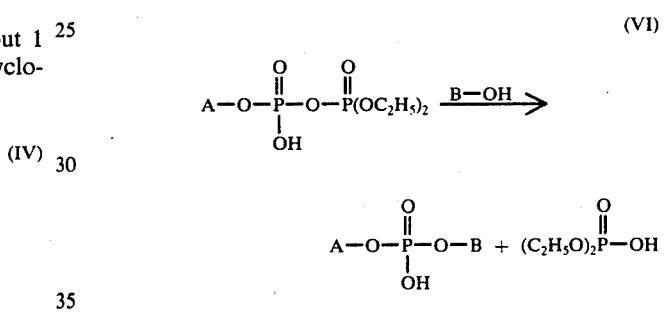

The diphosphoric acid triesters of formula (VI) are prepared according to methods known per se, see for instance the first reference given above (p. 895).

e. The compounds having formula (I) above of the present invention may also be prepared by the method described by J. Reiss in Bull. Soc. Chim. France 1965 p. 29 from a primary phosphoric acid ester of A—OH according to the reaction steps shown below

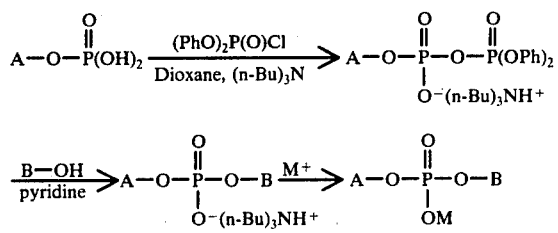

f. The compounds having formula (I) above of the invention may also be prepared by using 2-chloromethyl-4-nitrophenyl phosphorodichloridate in the reaction steps shown below, according to the method described by T. Hata et al. in Tetrahedron letters p. 3505 (1970).

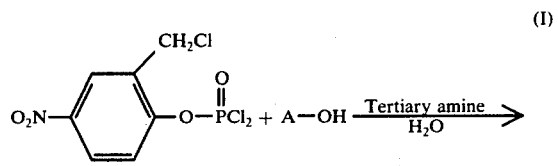

-continued

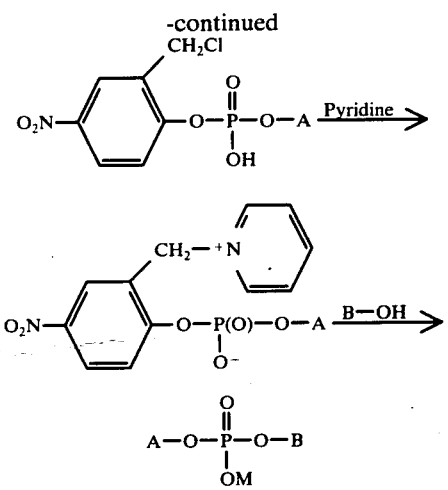

g. The compounds having formula (I) above may also be prepared by converting, in a manner known per se, derivatives thereof, for instance tertiary esters with a lower aliphatic alcohol, a phosphoric acid diester amide or a phosphoric acid diester halogenide, to secondary phosphoric acid esters of formula (I). This may be illustrated by the following reaction formulas, wherein A and B have the above meaning.

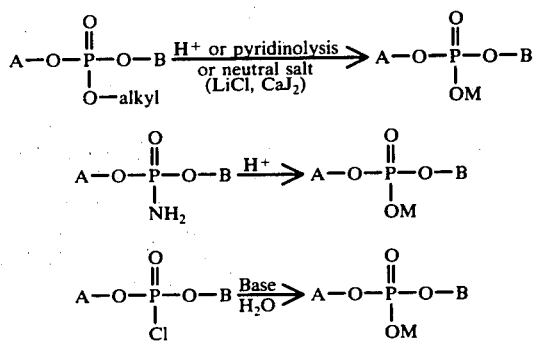

h. The compounds having the formula (I) may also be prepared according to Houben-Hoesch reaction (Friedel-Craft and Related Reactions III, 383, Interscience, New York, 1964) by reacting a compound

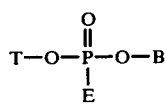

wherein T is

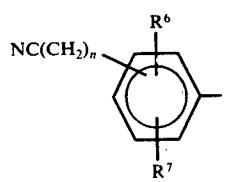

wherein $R^6$ and $R^7$ are different from R and n = 0 - 3 and wherein E is or by conventional methods can be transformed to —OM; with a compound -continued

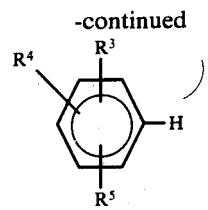

(VII)

in which at least two of the substituents $R^3$, $R^4$ and $R^5$ are selected from —OH and —OCH$_3$ and located in m-position to each other, under formation of a compound (I) in which X is

and $R^3$, $R^4$ and $R^5$ are the same as in the compound (VII) used.

i. The compounds having the formula (I) may also be prepared according to the schematic reaction indicated below.

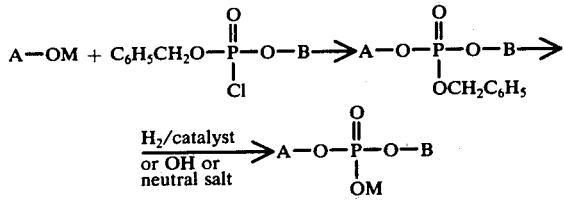

j. It is also possible to prepare the compounds having formula (I) according to the present invention by first preparing a secondary phosphoric acid ester, wherein one or several of the substituents $R^3$, $R^4$, $R^5$, $R^6$, $R^7$, $R^8$, $R^9$, $R^{10}$, $R^{11}$, $R^{12}$, $R^{13}$, $R^{14}$, consist of other groups than those desired, and then converting such groups in a manner known per se into the groups defined by the general formula (I).

As examples of such transformations, besides that mentioned in h above, the removing of protecting groups, e.g. benzyl-, trityl-, methoxymethyl-, tetrahydropyranyl-, trimethylsilyl-, carboalkoxy-, carbobenzoxy-, and benzoyl groups, may be mentioned.

k. It is also possible in a manner known per se to prepare compounds having the general formula (I) from other compounds within the definition of the general formula (I).

As examples of such transformations the following methods may be mentioned: Free hydroxyl groups are e.g. obtained by removal of acyl- and dihydroxy-phosphinyl groups from acyl esters and primary phosphoric acid esters, respectively, by removal of lower alkyl groups from lower alkoxy groups, and via diazonium salts from primary aromatic amines. Free amino groups are e.g. obtained by removal of acyl groups in acylamides, by reduction of nitro-, nitrile- and amide groups. Free carboxylic acid groups are e.g. obtained by hydrolysis of ester-, amide- and nitrile groups. On the other hand free hydroxy groups can be esterified and etherified, primary and secondary amines acylated to amides, and carboxylic acids esterified and also transformed to amides. By Mannich reaction it is possible to insert aminomethyl groups, and by Schiemann and Sandmayer reactions primary aromatic amines can be converted to fluor-, chloride- or nitrile groups.

As far as the group X is concerned examples of transformations which can be done within this group are found below when the methods to prepare (II) are exemplified.

1. If the secondary phosphoric acid esters having the above formula (I) are isolated in the form of the free acids, such acids can be transferred to salts with pharmaceutically acceptable inorganic or organic cations in a conventional way. Examples of suitable inorganic and organic cations are found above.

When a secondary phosphoric acid ester according to this invention is isolated in the form of a salt with a cation, which is not pharmaceutically acceptable, such salt is transferred to the free acid or to salts with pharmaceutically acceptable cations according to methods known per se, for instance by treatment of a salt with a strong acid, by using a suitable ion exchanger or by carrying out a double decomposition in a suitable solvent.

The methods used when synthetizing the secondary phosphoric acid esters of the invention have to be chosen in such a way that all groups in the starting materials involved are compatible with the method used or, if necessary, sensitive groups are protected during the reaction and then converted to the desired groups so that compounds of the general formula (I) above are obtained.

The hydroxy compounds (II), or functional derivatives thereof, used as starting materials in the preparation of the secondary phosphoric acid esters of the general formulas (II) and (III), are prepared according to known methods. Among useful methods to prepare these compounds, having two benzene rings connected with the group X or a group $R^{25}$, different from X, which can be converted to the group X by known methods at any suitable stage during the preparation of the secondary phosphate esters, the following types of reactions may be mentioned: Acetoacetic ester synthesis, Claisen-Schmidt condensation, Friedel-Crafts reaction, Fries rearrangement, Grignard reaction, Houben-Hoesch reaction, Knoevenagel condensation, Malonic ester synthesis, Necki reaction and Wittig reaction.

In all these types of reactions, appropriately substituted benzene compounds are used to form the compounds (II) a functional derivative thereof, or a compound having two appropriately substituted benzene rings connected to each other by a group $R^{25}$, which by conventional methods in one or more reaction steps, can be converted to the desired compound (II) or a functional derivative thereof.

As examples of transformations in the group X (or $R^{25}$) the following reactions can be mentioned.

Double bonds in X (or $R^{25}$) can be formed by elimination reactions. They can be hydrogenated catalytically, also in the presence of the carbonyl group, or new substituents can be inserted by addition reactions.

If $R^{25}$ carries a suitable hydroxylgroup such group can be converted to a carbonyl group by an oxidizing agent, e.g. an Oppenauer oxidation or a Sarett oxidation.

To insert groups like lower alkyl, phenyl and benzyl in X (or $R^{25}$) methods are found in references given below or in the examples of preparation.

Further details about the name reactions mentioned above are found e.g. in The Merck Index, 8th Ed., 1968, in the topic "Organic name reactions", p. 1137, and in references given there. Other references to these and other useful methods are found in reviews such as: Ind. Chim.Belg. (1961) 345; Organic Reactions 18 (1970) 1; and in monographs such as: T. A. Geismann, "The Chemistry of Flavonoid Compounds" (New York, 1962), p. 286; G. A. Olah, "Friedel-Crafts and Related Reactions", vol. II, part 1, and vol. III, part 1 (New York, 1964); and C. A. Buchler, D. E. Pearson, "Survey of Organic Syntheses" (New York, 1970), p. 623.

The reactions mentioned above to prepare (II) above, or functional derivatives thereof, are carried out in such a manner that each group of the compounds involved is compatible with the process in question or protected when necessary.

When the compound (II) above also carry other reactive groups such as —OH, primary and secondary amines and carboxylic acids, these groups are, when necessary, protected during the synthesis of the phosphate esters. Suitable protecting groups for —OH and amines are found in the monographs, S. Patai, "The Chemistry of the Hydroxyl Group" (London, 1971), p. 1001, and S. Patai "The Chemistry of the Amino Group" (London, 1968), p. 669. A free carboxylic acid group can, for instance, be protected by converting it to a suitable ester. Such protecting group or groups can then be removed at any suitable stage during the preparation of the secondary phosphoric acid esters.

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in anyone of various ways, for example orally as in capsules or tablets, parenterally in the form of sterile solutions, suspensions and by pellet implantation. Among routes of parental administration are intravenously, subcutaneously, intramuscularly, intraperitoneally, intraarticularly, intradermally and subconjunctivally. Other modes of administration are lingually, vaginally, rectally, by aerosol and topically as e.g. in the form of ointments, eye-drops, etc.

As representatives of living animal bodies, which may be treated with the compounds and compositions of the invention, and according to the method of treatment of the invention, for alleviation of the same and/or similar conditions as those described, the following may be mentioned:

domestic animals such as dogs and cats, farm animals such as horses, cows, sheep and goats, Pharmaceutcial formulations are usually prepared from a predetermined quantity of one or more of the compounds of the invention. Such formulations may take the form of powders, syrups, suppositories, ointments, eye-drops, elixirs, solutions, aerosls, pills, capsules, pellets or tablets, suspensions, emulsions, oil solutions etc., with or without, but preferably with, any one of a large variety of pharmaceutically acceptable vehicles or carriers. When in admixture with a pharmaceutical vehicle or carrier, the active ingredient usually comprises from about 0.01 to about 75 percent, normally from about 0.05 to about 15 percent, by weight of the composition. Carriers such as starch, sugar talc, commonly used synthetic and natural gums, water, and the like, may be used in such formulations. Binders such as polyvinylpyrrolidone and lubricants such as sodium stearate, may be used to form tablets. Disintegrating agents such as sodium bicarbonate may also be included in tablets.

Although relatively small quantities of the active materials of the invention, even as low as 5.0 milligrams, may be used in cases of administration to subjects having a relatively low body weight, unit dosages are preferably 5 milligrams or above and preferably 25, 50, or 100 milligrams, or even higher, depending of course upon the subject treated and the particular result desired, as will be apparent to one skilled in the art. Broader ranges appear to be 0.1 to 3000 milligrams per unit dose. The active agents of the invention may be combined for administration with other pharmacologically active agents such as natural or synthetic prostaglandins or analogues, antiseptics, spasmolytics, analgesics, tranquillizers, steroids or hormones, or the like, or with buffers, antacids or the like, and the proportion of the active agent or agents in the compositions may be varied widely. It is only necessary that the active ingredient of the invention constitutes an effective amount, i.e. such that a suitable effective dosage will be obtained consistent with the dosage form employed. Obviously, several unit dosage forms may be administered at about the same time. The exact individual dosages as well as daily dosages in a particular case will of course be determined according to well established medical and/or veterinary principles. As a rule, however, when used therapeutically, the present compounds may be administered in a quantity of 1 to 1000 milligrams per day and subject, divided in 1 or more doses, over a suitable period.

The following examples are intended to illustrate but not to limit the scope of the invention.

EXAMPLE 1

2.64 g of the 4-(2,4,6-trimethoxybenzoyl)phenyl dihydrogen phosphate obtained according to Example 20 is dissolved in dry pyridine (20 ml) and the pyridine then evaporated in vacuo. This drying process is repeated twice and the residue is then dissolved in dry pyridine (30 ml) and triethylamine (2.02 ml) and 1,3,5-triisopropylbenzenesulphonyl chloride (4.46 g) added. After two hours at room temperature phenol is added (0.69 g) and the reaction mixture left for 70 hours at room temperature. Water is then added and the resulting solution poured in an excess of 2 M hydrochloric acid. The resulting precipitate is collected and dissolved in ethanol:water with sodium hydroxide to a pH-value of about 5. An amount of 0.4 M acetate buffer, pH 5, coresponding to about half the volume of the reaction mixture is added and the resulting mixture is boiled for 15 hours so that all unreacted monophosphate is hydrolyzed. The unphosphorylated product is removed by extraction with ether and a pure (TLC) product is obtained by precipitation with hydrochloric acid and washing the obtained product with water. The substance is dissolved in acetone:water with sodium hydroxide to a pH-value of about 4. Most of the acetone is removed in vacuo and the remaining water solution freeze-dried.

The salt obtained is sodium 4-(2,4,6-trimethoxybenzoyl)phenyl phenyl phosphate.

By substituting phenol above with an alcohol the following ester is prepared:
sodium 4-(2,4,6-trimethoxybenzoyl)phenyl propyl phosphate.

EXAMPLE 2

4.9 g 4-(3-oxo-3-(2,4,6-tribenzoyloxyphenyl)propyl)-phenyl dihydrogen phosphate obtained according to Example 20 is dissolved in 15 ml dry pyridine. Trichloroacetonitrile (14.4 g) and ethanol (0.92 g) are added and the reaction mixture is heated to 90° C for 3 hours. After evaporation in vacuo the residue is dissolved in butanone and poured on a mixture of diluted hydrochloric acid and ethyl acetate. The organic layer is washed with water, neutralized to pH 5 and evaporated. The residue is dissolved in 300 ml of methanol. 15 ml of deaired 2 M sodium hydroxide is added and the mixture is kept at 20° C under nitrogen for 10 min. The pH of the solution B adjusted to 4, the solvent is evaporated. 150 ml of water is added and extracted with 300+150+100 ml of diethyl ether. The aqueous phase is freeze-dried. The product is dissolved in 100 ml of acetone, filtered and evaporated. The residue is acidified with diluted hydrochloric acid and extracted with ethyl acetate. Water is added to the ethyl acetate solution and pH is adjusted to 5 with 1 M sodium hydroxide solution. The solution is freeze-dried giving sodium ethyl 4-(3-oxo-3-(2,4,6-trihydroxyphenyl)propyl)phenyl phosphate, pure in TLC and giving a NMR-spectrum confirming its structure.

By replacing ethanol with other alcohols the following compounds are obtained
sodium methyl 4-(3-oxo-3-(2,4,6-trihydroxyphenyl)propyl)phenyl phosphate and
sodium cyclohexyl 4-(3-oxo-3-(2,4,6-trihydroxyphenyl)propyl)phenyl phosphate.
sodium n-hexyl 4-(3-oxo-3-(2,4,6-trihydroxyphenyl)propyl)phenyl phosphate In substantially the same manner, but omitting the treatment with methanol and sodium hydroxide there is obtained sodium 1-hexyl 4-(3-oxo-3-phenylpropyl)phenyl phosphate from 1-hexanol and 4-(3-oxo-3-phenylpropyl)phenyl dihydrogen phosphate.
sodium 4-benzoyl-2,6-dimethylphenyl cyclohexyl phosphate from 4-benzoyl-2,6-dimethylphenyl dihydrogen phosphate and cyclohexanol
sodium 4-(2,4,6-trimethoxybenzoyl)phenyl n-octyl phosphate from 4-(2,4,6-trimethoxybenzoyl)phenyl dihydrogen phosphate and n-octanol
sodium 4-(2,4,6-trimethoxybenzoyl)phenyl propyl phosphate from 4-(2,4,6-trimethoxybenzoyl)phenyl dihydrogen phosphate and 1-propanol
sodium 4-(2,4,6-trimethoxybenzoyl)phenyl ethyl phosphate from 4-(2,4,6-trimethoxybenzoyl)phenyl dihydrogen phosphate and ethanol.
sodium n-hexyl 4-(3-oxo-3-(2,4,6-trimethoxyphenyl)propyl)phenyl phosphate from 4-(3-oxo-(3-(2,4,6-trimethoxyphenyl)propyl)phenyl dihydrogen phosphate and n-hexanol
sodium 3,7-dimethyloctyl 4-(3-oxo-3-(2,4,6-trimethoxyphenyl)propyl)phenyl phosphate from 4-(3-oxo-(3-(2,4,6-trimethoxyphenyl)propyl)phenyl dihydrogen phosphate and 3,7-dimethyloctanol.
sodium 4-(2,4,6-trimethoxybenzoyl)phenyl 4-tert.-butylcyclohexyl phosphate from 4-(2,4,6-trimethoxybenzoyl)phenyl dihydrogen phosphate and 4-tert.-butylcyclohexanol.

EXAMPLE 3

A solution of 6.3 g of 4'-hydroxy-2',6'-dimethoxy-3-(4-methoxyphenyl)propiophenone in 70 ml dry pyridine is slowly added (20 min) with stirring to a solution of 21.1 g phenyl phosphorodichloridate in 50 ml dry pyridine at a temperature of −10° C. After an additional hour the temperature is kept at 0° C for one hour and then at room temperature until the next day. The reaction mixture is poured on crushed ice (95 g) and the resulting solution evaporated in vacuo to a volume of about 75 ml. The residue is poured into a mixture of 5 M hydrochloric acid (50 ml) and ice (100 g). The precipitate formed is extracted with ethyl acetate. The organic phase is washed with water and dried with magnesium sulphate. The solvent is evaporated at reduced pressure. The residue is mixed with 100 ml of water and dissolved by addition of 1 M sodium hydroxide to pH 5. After extraction with ether the aqueous phase is freeze-dried giving sodium 3,5-dimethoxy-4-(3-(4-methoxyphenyl)-propionyl)phenyl phenyl phosphate, pure according to TLC. The structure is confirmed by NMR.

In substantially the same manner there is obtained from phenyl phosphorodichloridate, with the phenyl group unsubstituted or substituted as necessary for the phosphates mentioned below, and from hydroxy-substituted 3-phenylpropiophenones and hydroxy-substituted 3-phenylacrylophenones, having the substituents required for the mentioned phosphates.

sodium 3,5-dimethoxy-4-(3-(4-methoxyphenyl)propionyl)phenyl 3,5-dimethylphenyl phosphate sodium phenyl 4-(3-oxo-3-(2,4,6-trimethoxyphenyl)-prooyl)phenyl phosphate sodium 3,5-dimethoxy-4-(3-(4-methoxyphenyl)propionyl)phenyl phenyl phosphate sodium 3,5-dimethoxy-2-(3-(4-methoxyphenyl)propionyl)phenyl phenyl phosphate Each of the phenyl propiophenones used for these four phosphates are obtained from a 3-phenylpropionitril and a methyl phenyl ether, both being substituted in the benzene rings in such a way that the desired end product is obtained, in substantially the manner described in J. Chem. Soc. 1930, 21.

sodium 4-fluorophenyl 4-(2,3-diphenyl)acryloyl)-3-methoxyphenyl phosphate sodium 4-(3-(4-carboxyphenyl)-2-(4-methoxyphenyl)acryloyl)-3-methoxyphenyl phenyl phosphate The starting materials for the syntheses are obtained by condensation of benzaldehyde with 4'-hydroxy-2'-methoxy-2-phenylacetophenone and by condensation of 4-formylbenzoic acid with 4'-hydroxy-2'-methoxy-2-(4-methoxyphenyl)acetophenone in substantially the same manner described in J. Pr. Chem. (2) 159, 273 (1942).

sodium 3,5-dimethylphenyl 3-(2-(2-hydroxybenzoyl)-n-butyl)-phenyl phosphate sodium 3-(2-benzoyl-3-phenylpropyl)phenyl phenyl phosphate sodium 3-(2-benzoyl-3-(4-chlorophenyl)propyl)phenyl phenyl phosphate sodium 4-(2-benzyl-n-hexanoyl)phenyl phenyl phosphate sodium 4-(2-benzyl-3-(4-fluorophenyl)propionyl)phenyl phenyl phosphate sodium 3-(3-oxo-3-phenyl-2-(3-trifluoromethylphenyl)-propyl)phenyl phenyl phosphate The starting materials for the above six phosphates are obtained from 2'-methoxy-3-(3-methoxyphenyl)-propiophenone and ethyl bromide, from 3-(3-methoxyphenyl)-propiophenone and 4-chlorobenzyl chloride, from 4'-methoxy-3-phenylpropiophenone and butylbromide, 4'-methoxy-3-phenylpropiopenone and 4-fluorobenzyl chloride, and 3-(3-methoxyphenyl)propiophenone and 3-trifluoromethylbenzyl chloride respectively by reaction which for each set of compounds involves first an alkylation in DMSO with potassium t-butoxide as halogen acceptor, substantially as described in Fieser and Fieser, Reagents for Org. Synth., Wiley, New York, 1967, p. 915 and then a demethylation using pyridine hydrochloride substantially in the manner described in Houben-Weyl, Methoden der Organischen Chemie, Vol. 6/3, p. 152.

sodium 2,6-dimethoxyphenyl 3-(2,3-diphenyl-3-oxopropyl)phenyl phosphate

The starting material for this phosphate is obtained in the same manner as described from 2-phenylacetophenone and 3-methoxybenzyl chloride.

sodium 3-hydroxy-4-(4-phenylbutyryl)phenyl 3,5-dimethoxyphenyl phosphate from 2',4'-dihydroxy-4-phenylbutyrophenone, obtained from 3-cyanopropylbenzene and resorcinol in substantially the manner described for related compounds in Friedel-Crafts and Related Reactions III, Interscience, New York, 1964, p. 383.

sodium 4-(3-(2-hydroxyphenyl)-3-oxopropyl)phenyl phenyl phosphate sodium 3,5-dimethylphenyl 3-(3-(2-hydroxyphenyl)-3-oxopropyl)phenyl phosphate sodium 2-isopropylphenyl 4-(3-oxo-3-phenylpropyl)-phenyl phosphate sodium 2-naphthyl 4-(3-oxo-3-phenylpropyl)phenyl phosphate sodium 4-(2-butyl)phenyl 4-(3-oxo-3-phenylpropyl)phenyl phosphate sodium phenyl 3-(3-(2,4,6-trimethoxyphenyl)-3-oxopropyl)phenyl phosphate sodium 3-(3-(3,5-dimethyl-4-methoxyphenyl)-3-oxopropyl)phenyl phenyl phosphate sodium 2-(3-oxo-3-phenylpropyl)phenyl phenyl phosphate sodium 3,5-dimethoxyphenyl 2-methoxy-4-(3-(3-trifluoro-methylphenyl)-3-oxopropyl)phenyl phosphate sodium 3-(3-(4-cyanophenyl)acryloyl)phenyl 3-ethyl-5-methylphenyl phosphate sodium 4-(3-(3-nitrophenyl)-3-oxopropenyl)phenyl phenyl phosphate sodium 4-(3-oxo-3-phenylpropyl)phenyl phenyl phosphate sodium 2-methylphenyl 4-(3-oxo-3-phenylpropyl)phenyl phosphate sodium 3-methylphenyl 4-(3-oxo-3-phenylpropyl)phenyl phosphate sodium 4-methylphenyl 4-(3-oxo-3-phenylpropyl)phenyl phosphate sodium 4-ethylphenyl 4-(3-oxo-3-phenylpropyl)phenyl phosphate sodium 3-ethyl-5-methylphenyl 4-(3-oxo-3-phenylpropyl)phenyl phosphate sodium 2,6-dimethylphenyl 4-(3-oxo-3-phenylpropyl)-phenyl phosphate sodium 2-nitrophenyl 4-(3-oxo-3-phenylpropyl)phenyl phosphate sodium 4-nitrophenyl 4-(3-oxo-3-phenylpropyl)phenyl phosphate sodium 2,6-dimethyl-4-(3-oxo-3-phenylpropyl)phenyl phenyl phosphate sodium 2-(3-oxo-3-phenylpropenyl)phenyl phenyl phosphate sodium 4-(3-phenylpropionyl)phenyl phenyl phosphate sodium 4-(3-(4-n-butoxyphenyl)-3-oxopropyl)phenyl phenyl phosphate disodium 4-(3-(4-carboxylatomethyl-phenyl)-3-oxopropyl)phenyl 3,5-dimethylphenyl phosphate sodium 4-(3-(4-ethoxycarbonylmethyl-phenyl)-3-oxopropyl)phenyl phenyl phosphate sodium 4-(3-(4-fluorophenyl)-3-oxopropyl)phenyl phenyl phosphate sodium 4-(3-(4-N,N-dimethylcarbamoylmethylphenyl)-3-oxopropyl) phenyl 3,5-dimethylphenyl phosphate sodium 4-(3-(4-fluorophenyl)-3-oxopropenyl)phenyl phenyl phosphate sodium 3-(3-(4-carboxyphenyl)propionyl)phenyl 3-chlorophenyl phosphate sodium 3-(3-(4-isopropylphenyl)propionyl)phenyl phenyl phosphate sodium 3-nitrophenyl 4-(3-oxo-3-phenylpropyl)phenyl phosphate sodium 3,5-dimethylphenyl 4-(3-oxo-3-phenylpropyl)phenyl phosphate sodium 1-naphthyl 4-(3-oxo-3-phenylpropyl)phenyl phosphate sodium 3,5-dimethylphenyl 2-(3-phenylacryloyl)phenyl phosphate sodium 4-(3-oxo-3-phenylpropyl)phenyl 4-biphenylyl phosphate ethylene ketal of sodium phenyl 4-(3-oxo-3-phenylproyl)phenyl phosphate sodium 3,5-dimethylphenyl 3-(3-oxo-3-phenylpropyl)phenyl phosphate sodium phenyl 4-(3-oxo-3-phenyl-1-propenyl)phenyl phosphate The starting materials for this group of phosphates are obtained from pairs of benzaldehyde and acetophenone suitably substituted to give the desired product, by condensation and, for the formation of 3-phenylpropiophenones by hydrogenation, by applying the methods desired in Example 19.

In substantially the same manner the following secondary phosphoric acid esters are prepared (and isolated as free acids) from substituted or unsubstituted aryl phosphorodichloridates and a monophenolic compound (given below). The different substituted or unsubstituted aryl phosphorodichloridates which are used as starting material will be clearly understood from the names of the endproducts mentioned below.

4-(2-methoxycarbonyl benzoyl) phenyl phenyl hydrogen phosphate from methyl 2-(4-hydroxybenzoyl) benzoate.

4-benzoyl-3-butoxycarbonylmethoxyphenyl 3,5-dimethyl phenyl hydrogen phosphate from 2-butoxycarbonylmethoxy-4-hydroxy-benzophenone (which is obtained by esterification of 3-hyroxy-phenoxyacetic acid with n-butanol, followed by Friedel-Craft reaction of the obtained ester with benzoyl chloride.

4-(2-butoxycarbonylbenzoyl) phenyl phenyl hydrogen phosphate from 2'-butoxy-carbonyl-4-hydroxybenzophenone which is obtained from 2'-carboxy-4-hydrocarbenzophenone by esterification with n-butyl alcohol.

4-benzoyl-3-butoxycarbonyl methyl phenyl 3,5-dimethyl phenyl hydrogen phosphate from 2-butoxycarbonylmethyl-4-hydroxybenzophenone which is obtained by esterification of 3-hydroxyphenylacetic acid with n-butyl alcohol, followed by Friedel-Craft reaction of the obtained ester with benzoyl chloride.

4-benzoyl-3-methoxycarbonylphenyl 3,5-dimethylphenyl hydrogen phosphate from methyl 2-benzoyl-5-hydroxybenzoate (which is obtained from 2-benzoyl-5-hydroxybenzoic acid by esterification with methanol).

2-benzoyl-4-methoxycarbonylphenyl phenyl hydrogen phosphate from methyl 3-benzoyl-4-hydroxybenzoate. phenylacetate and benzoyl chloride).

2-benzoyl-4-methoxycarbonylmethylphenyl 3,5-dimethyl-phenyl hydrogen phosphate from methyl 3-benzoyl-4-hydroxyphenylacetate (which is obtained from Friedel-Craft reaction between methyl 4-hydroxyphenylacetate and benzoyl chloride).

4-benzoyl-3-methoxycarbonylmethoxyphenyl 3,5-dimethyl-phenyl hydrogen phosphate from methyl 2-benzoyl-5-hydroxy-phenoxyacetate (which is obtained from Friedel-Craft reaction between methyl 3-hydroxyphenoxyacetate and benzoyl chloride).

3-benzoyl-4-methoxycarbonylmethoxyphenyl phenyl hydrogen phosphate from methyl 2-benzoyl-4-hydroxyphenoxyacetate (which obtained by esterification of 4-hydroxyphenoxyacetic acid with methanol, followed by Friedel-Craft reaction of the obtained methyl ester with benzoyl chloride).

2-benzoyl-4-methoxycarbonylmethoxyphenyl phenyl hydrogen phosphate from methyl 3-benzoyl-4-hydroxyphenoxyacetate (which is obtained by esterification of 4-hydroxyphenoxyacetic acid with methanol, followed by Friedel-Craft reaction of the obtained methyl ester with benzoyl chloride).

sodium 3-(2,4,6-trimethylbenzoyl)phenyl 4-methoxycarbonylphenyl phosphate from 3-hydroxy-2',4',6'-trimethylbenzophenone (which is obtained from Friedel-Craft reaction between mesitylene and m-methoxybenzoyl chloride, followed by demethylation with pyridine hydrobromide) and 4-methoxycarbonylphenyl phosphorodichloridate (which is obtained from methyl 4-hydroxybenzoate and phosphorus oxychloride).

4-(2-methoxycarbonylbenzoyl)phenyl 3,5-dimethyl phenyl hydrogen phosphate from methyl 2-(4-hydroxybenzoyl)benzoate.

4-benzoyl-3-methoxycarbonylmethylphenyl 3,5-dimethyl-phenyl hydrogen phosphate from methyl 2-benzoyl-5-hydroxyphenylacetate (which is obtained from Friedel-Craft reaction between methyl 3-hydroxy In substantially the same manner the following sodium salts of secondary phosphoric acid esters are prepared.

sodium 4-(4-methoxybenzoyl)-3,5-dimethoxyphenyl phenyl phosphate from 4-hydroxy-2,4',6-trimethoxybenzophenone (which is obtained from Houben-Hoesch reaction between p-methoxybenzonitrile and 3,5-dimethoxyphenol).

sodium 4-benzoyl -3-methoxyphenyl phenyl phosphate from 4-hydroxy-2-methoxy-benzophenone.

sodium 4-benzoyl-3,5-dimethoxyphenyl phenyl phosphate from 4-hydroxy-2,6-dimethoxy-benzophenone.

sodium 3-methoxy-4-(4-methoxybenzoyl) phenyl phenyl phosphate from 4-hydroxy-2,4'-dimethoxybenzophenone (which is obtained from Friedel-Craft reaction between m-methoxyphenol and p-methoxybenzoyl chloride).

sodium 4-(3,5-dimethylbenzoyl)phenyl phenyl phosphate from 4-hydroxy-3',5'-dimethylbenzophenone (which is obtained from Friedel-Craft Craft reaction between anisol and 3,5-dimethylbenzoyl chloride followed by demethylation with pyridine hydrobromide).

sodium 2,6-dimethoxy-4-(2,4,6-trimethoxybenzoyl)phenyl phenyl phosphate from 4-hydroxy-2',3,4',5,6'-pentamethoxybenzophenone (which is obtained from Friedel-Craft reaction between 2,6-dimethoxyphenol and 2,4,6-trimethoxybenzoyl chloride).

sodium 3-(2,4,6-trimethoxybenzoyl)phenyl phenyl phosphate from 3-hydroxy-2',4',6'-trimethoxybenzophenone (which is obtained from Houben-Hoesch reaction between 1,3,5-trimethoxybenzene and m-hydroxybenzonitrile).

sodium 4-(2-oxo-2-(2,4,6-trimethoxyphenyl)ethyl)phenyl phenyl phosphate from 4'-hydroxy-2,4,6-trimethoxydeoxybenzoin (which is obtained from Hoesch reaction between 1,3,5-trimethoxybenzene and p-hydroxybenzyl cyanide).

sodium ethylene ketal of 4-(phenylacetyl)phenyl phenyl phosphate from 4-hydroxydeoxybenzoin in the form of its ethylene ketal which is prepared from 4-hydroxydeoxybenzoin and ethylene glycol in benzene with azeotropic distillation of water.

sodium 4-(4-cyanobenzoyl)-phenyl phenyl phosphate from 4-(4-cyanobenzoyl)phenol sodium 4-(3-fluorobenzoyl)-2,5-dimethylphenyl phenyl phosphate from 3'-fluoro-4-hydroxy-2,5-dimethylbenzophene (which is obtained from Friedel-Craft reaction between 2,5-dimethylphenol and m-fluorobenzoyl chloride).

sodium 4-(bis(2-(4-chlorophenyl)acetyl)phenyl phenyl phosphate from bis(2-(4-chlorophenyl)-4'-hydroxyactophenone (which is obtained from Friedel-Crafts reaction between bis(4-chlorophenyl)acetyl chloride and anisol followed by demethylation with pyridine hydrobromide).

sodium 2-acetylaminomethyl-4-benzoyl-6-methylphenyl phenyl phosphate from 3-acetylaminomethyl-4-hydroxy-5-methyl-benzophenone.

sodium 2-diethylaminomethyl-4-benzoyl-6-methylphenyl phenyl phosphate from 3-diethylaminomethyl-4-hydroxy-5-methyl-benzophenone.

sodium 3(2,5-dimethylbenzoyl)phenyl phenyl phosphate from 3-hydroxy-2',5'-dimethylbenzophenone (which is obtained from Friedel-Craft reaction between p-xylene and m-methoxybenzoyl chloride, followed by demethylation with pyridine hydrobromide).

sodium 3-(2,4,6-trimethylbenzoyl)phenyl phenyl phosphate from 3-hydroxy-2',4',6'-trimethylbenzophenone (which is obtained from Friedel-Craft reaction between mesitylene and m-methoxybenzoyl chloride, followed by demethylation with pyridine hydrobromide).

sodium 4-(2-cyclohexyl-1-oxo-2-phenylethyl)phenyl phenyl phosphate from 2-cyclohexyl-1-(4-hydroxyphenyl)-2-phenylethanone (which is obtained by treatment of 4-methoxy deoxybenzoin with cyclohexylbromide in the presence of sodium ethylate followed by demethylation with pyridine hydrobromide).

sodium 4-(1-oxo-2,2-diphenylethyl)phenyl phenyl phosphate from 1(4-hydroxyphenyl)-2,2-diphenylethanone.

sodium 4-(2-(3-methylphenyl)-2-(4-methylphenyl)acetyl)phenyl)phenyl phosphate from 4'-hydroxy-2-(3-methylphenyl)-2-(4-methylphenyl)acetophenone (which is obtained from (3-methylphenyl)-(4-methylphenyl)acetyl chloride and anisol in Friedel-Crafts reaction and then demethylated with pyridine hydrobromide.

sodium 4-(2,4,6-trimethylbenzoyl)phenyl phenyl phosphate from 4-hydroxy-2',4',6'-trimethyl-benzophenone (which is obtained from Friedel-Craft reaction between mesitylene and p-methoxybenzoylchloride, followed by demethylation with pyridine hydrobromide).

sodium 4-(2,5-dimethylbenzoyl)-2,6-dimethylphenyl phenyl phosphate from 4-hydroxy-2',3,5,5'-tetramethyl-benzophenone (which is obtained from Friedel-Craft reaction between 2,6-dimethylphenol and 2,5-dimethylbenzoylchloride).

sodium 4-(2,4-dimethylbenzoyl)-2,6-dimethylphenyl phenyl phosphate from 4-hydroxy-2',3,4',5-tetramethyl-benzophenone (which is obtained from Friedel-Craft reaction between 2,6-dimethylphenol and 2,4-dimethylbenzoyl chloride).

sodium 4-(3,5-dimethylbenzoyl)-2,6-dimethylphenyl phenyl phosphate from 4-hydroxy-3,3',5,5'-tetramethyl-benzophenone (which is obtained from Friedel-Craft reaction between 2,6-dimethylphenol and 3,5-dimethyl benzoylchloride).

sodium 4-benzoyl-2,3,5,6-tetramethylphenyl phenyl phosphate from 4-hydroxy-2,3,5,6-tetramethyl-benzophenone (which is obtained from Friedel-Craft reaction between 2,3,5,6-tetramethylphenol and benzoylchloride).

sodium 4-benzoyl-2,6-di-t-butylphenyl phenyl phosphate from 4-hydroxy-3,5-di-t-butyl-benzophenone.

sodium 4-benzoyl-2-t-butyl-6-methylphenyl phenyl phosphate from 4-hydroxy-3-t-butyl-5-methyl-benzophenone (which is obtained by treating the Na-salt of 2-tert.-butyl-6-methylphenol with benzoyl chloride in dioxane).

sodium 4-(2,4-dimethylbenzoyl)-2,6-dimethoxyphenyl phenyl phosphate from 4-hydroxy-3,5-dimethoxy-2',4'-dimethyl-benzophenone (which is obtained directly from Friedel-Craft reaction between m-xylene and 3,4,5-trimethoxy benzoyl chloride).

sodium 4-benzoyl-2-propionylphenyl phenyl phosphate from 4-hydroxy-3-propionyl-benzophenone (which is obtained from Friedel-Craft reaction between o-hydroxypropionphenone and benzoylchloride), sodium 4-(3,5-dimethoxybenzoyl)phenyl phenyl phosphate from 4-hydroxy-3',5'-dimethoxy-benzophenone (which is obtained from Friedel-Craft reaction between phenol and 3,5-demethoxybenzoyl chloride).

sodium 4-(3,5-dimethoxybenzoyl)-2,6-dimethylphenyl phenyl phosphate from 4-hydroxy-3',5'-dimethoxy-3,5-dimethyl-benzophenone (which is obtained from Friedel-Craft reaction between, 2,6-dimethylphenol and 3,5-dimethoxybenzoyl chloride.

sodium 4-benzoyl-2-bromophenyl phenyl phosphate from 3-bromo-4-hydroxy-benzophenone.

sodium 4-benzoyl-2,6-dibromophenyl phenyl phosphate from 3,5-dibromo-4-hydroxy-benzophenone.

sodium 4-benzoyl-2-chlorophenyl phenyl phosphate from 3-chloro-4-hydroxy-benzophenone.

sodium 4-(2-bromobenzoyl)phenyl phenyl phosphate from 2'-bromo-4-hydroxybenzophenone.

sodium 3-(4-methylbenzoyl)phenyl phenyl phosphate from 3-hydroxy-4'-methyl-benzophenone (which is obtained from Friedel-Craft reaction between toluene and m-methoxybenzoyl chloride, followed by demethylation with pyridine hydrobromide).

sodium 3-(2,3,5,6-tetramethylbenzoyl)phenyl phenyl phosphate from 3-hydroxy-2',3',5',6'-tetramethyl-benzophenone (which is obtained from Friedel-Craft reaction between durene and m-methoxybenzoyl chloride, followed by demethylation with pyridine hydrobromide).

sodium 2-benzoyl-4,6-dimethylphenyl phenyl phosphate from 2-hydroxy-3,5-dimethyl-benzophenone.

sodium 2-(2,4-dimethylbenzoyl) phenyl phenyl phosphate from 2-hydroxy-2',4'-dimethyl-benzophenone.

sodium 2-benzoyl-4-chlorophenyl phenyl phosphate from 5-chloro-2-hydroxy-benzophenone.

sodium 2-benzoyl-4-nitrophenyl phenyl phosphate from 2-hydroxy-5-nitro-benzophenone.

sodium 3-methyl-4-phenylacetylphenyl phenyl phosphate from 4-hydroxy-2-methyl-deoxybenzoin.

sodium 2,6-dimethyl-4-phenylacetylphenyl phenyl phosphate from 4-hydroxy-3,5-dimethyl-deoxybenzoin (which is obtained from Friedel-Craft reaction between 2,6-dimethylphenol and phenylacetyl chloride).

sodium 4-(4-methoxyphenylacetyl) phenyl phenyl phosphate from 4-hydroxy-4-methoxy-deoxybenzoin (which is obtained by partial demethylation of 4,4'-dimethoxy-deoxybenzoin with hydrobromic acid).

sodium 4-phenylacetyl-2-propionyl phenyl phenyl phosphate from 4-hydroxy-3-propionyl-deoxybenzoin (which is obtained from Friedel-Craft reaction between o-hydroxypropionphenone and phenylacetylchloride).

sodium 3,5-dimethyl-2-phenylacetylphenyl phenyl phosphate from 2-hydroxy-4,6-dimethyl-deoxybenzoin (which is obtained from Friedel-Craft reaction between 3,5-dimethylphenol and phenylacetyl chloride).

sodium 5-methoxi-2-phenylacetylphenyl phenyl phosphate from 2-hydroxy-4-methoxy-deoxybenzoin.

sodium 4-isobutyl-2-phenylacetylphenyl phenyl phosphate from 2-hydroxy-5-isobutyl-deoxybenzoin (which is obtained from Friedel-Craft reaction between 4-sec.-butylphenol and phenylacetyl chloride).

sodium 4-(2,4-dimethoxybenzoyl) phenyl phenyl phosphate from 4-hydroxy-2',4'-dimethyoxybenzophenone (which is obtained from the reaction of 1,3-dimethoxybenzene and p-hydroxybenzoic acid in polyphosphoric acid).

sodium 4-(2-cyanobenzoyl) phenyl phenyl phosphate from 2'-cyano-4-hydroxybenzophenone (which is obtained from 2'-methoxycarbonyl-4-hydroxybenzophenone through 2'-carbamoyl-2-hydroxybenzophenone).

sodium 4-benzoyl-2,6-dimethylphenyl phenyl phosphate from 4-hydroxy-3,5-dimethyl-benzophenone In substantially the same manner the following compounds are obtained starting from 3-hydroxy-2',4',6'-trimethylbenzophenone (which is obtained from Friedel-Craft reaction between mesitylene and m-methoxybenzoyl chloride, followed by demethylation with pyridine hydrobromide), and a substituted aryl phosphorodichloridate give below.

sodium 3-(2,4,6-trimethylbenzoyl)phenyl-4-tert. butylphenyl phosphate from 4-tert. butylphenyl phosphorodichloridate.

sodium 3-(2,4,6-trimethylbenzoyl)phenyl 4-chlorophenyl phosphate from 4-chlorophenyl phosphorodichloridate.

sodium 3-(2,4,6-trimethylbenzoyl)phenyl 4-methoxyphenyl phosphate from 4-methoxyphenyl phosphorodichloridate.

sodium 3-(2,4,6-trimethylbenzoyl)phenyl 3-trifluoromethylphenyl phosphate from 3-trifluoromethylphenyl phosphorodichloridate.

sodium 3-(2,4,6-trimethylbenzoyl)phenyl 4-acetylphenyl phosphate from 4-acetylphenyl phosphorodichloridate (which is obtained by phosphorylation of 4-acetylphenol with phosphorus oxychloride).

sodium 3-(2,4,6-trimethylbenzoyl)phenyl 3-bromophenyl phosphate from 3-bromophenyl phosphorodichloridate (which is obtained by phosphorylation of 3-bromophenol with phosphorus oxychloride).

sodium 3-(2,4,6-trimethylbenzoyl)phenyl 4-fluorophenyl phosphate from 4-fluorophenyl phosphorodichloridate (which is obtained by phosphorylation of 4-fluorophenol with phosphorus oxychloride).

sodium 3-(2,4,6-trimethylbenzoyl)phenyl 4-phenylphenyl phosphate from 4-phenylphenyl phosphorodichloridate.

sodium 4-benzoyl-2,6-dimethylphenyl 2-naphtyl phosphate from 4-hydroxy-3,5-dimethylbenzophenone and 2-naphtyl phosphorodichloridate.

sodium 4-benzoyl-2,6-dimethylphenyl-1-naphtyl phosphate from 4-hydroxy-3,5-dimethylbenzophenone and 1-naphthyl phosphorodichloridate.

sodium 4-benzoyl-2,6-dimethylphenyl 2,6-dimethylphenyl phosphate from 4-hydroxy-3,5-dimethylbenzophenone and 2,6-dimethylphenyl phosphorodichloridate (which is obtained from 2,6-dimethylphenol and phosphorus oxychloride).

sodium 4-benzoyl-2,6-dimethylphenyl 3-nitrophenyl phosphate from 4-hydroxy-3,5-dimethylbenzophenone and 3-nitrophenyl phosphorodichloridate.

In substantially the same manner the following compounds are obtained starting from 3,5-dimethylphenyl phosphorodichloridate and monophenolic compounds given below.

sodium 2-allyl-4-benzoylphenyl 3,5-dimethylphenyl phosphate from 2-allyl-4-hydroxybenzophenone.

sodium 4-phenylacetyl-2-propionylphenyl 3,5-dimethylphenyl phosphate from 4-hydroxy-3-propionyl-deoxybenzoin (which is obtained from Friedel-Craft reaction between 2-hydroxypropiophenone and phenylacetylchloride).

sodium 4-(2-methoxy-1-oxo-2-phenylethyl)phenyl 3,5-dimethylphenyl phosphate from 1-(4-hydroxyphenyl)-2-methoxy-2-phenylethanone (which is obtained from 4-hydroxybenzoin by reaction with methanol).

sodium 4-benzoyl-3-methoxyphenyl 3,5-dimethylphenyl phosphate from 4-hydroxy-2-methoxy-benzophenone.

sodium 4-benzoyl-3,5-dimethoxyphenyl 3,5-dimethylphenyl phosphate from 4-hydroxy-3,5-dimethoxybenzophenone.

sodium 3,5-dimethoxy-4-(4-methoxybenzoyl) 3,5-dimethylphenyl phosphate from 4-hydroxy-2,4',6-trimethoxybenzophenone (which is obtained from Houben-Hoesch reaction between p-methoxybenzonitrile and 3,5-dimethoxyphenol).

sodium 4-(3-nitrobenzoyl)phenyl 3,5-dimethylphenyl phosphate from 3'-nitro-4-hydroxybenzophenone.

sodium 4-(4-nitrobenzoyl)phenyl 3,5-dimethylphenyl phosphate from 4-hydroxy-4'-nitro-benzophenone.

sodium 4-(4-trifluoromethylbenzoyl)phenyl 3,5-dimethylphenyl phosphate from 4-hydroxy-4'-trifluoromethylbenzophenone (which is obtained from Friedel-Craft reaction between phenol and 4-trifluoromethylbenzoyl chloride).

sodium 4-(2-(2,4,6-trimethoxyphenyl)-2-oxoethyl)phenyl 3,5-dimethylphenyl phosphate from 4'-hydroxy-2,4,6-trimethoxydeoxybenzoin (which is obtained from Hoesch reaction between 1,3,5-trimethoxybenzene and p-hydroxybenzyl cyanide).

sodium 4-phenylacetylphenyl 3,5-dimethylphenyl phosphate from 4-hydroxydeoxybenzoin.

sodium 4-benzoyl-2,6-dimethylphenyl 3,5-dimethylphenyl phosphate from 4-hydroxy-3,5-dimethylbenzophenone.

sodium 2-benzoyl-3,5-dimethylphenyl phenyl phosphate from 2-hydroxy-4,6-dimethylbenzophenone (which is obtained from Friedel-Craft reaction between 3,5-dimethylphenol and benzoyl chloride).

sodium 4-(2-cyano-1-oxo-2-phenylethyl) phenyl 3,5-dimethyl phenyl phosphate from 2-cyano-1-(4-hydroxyphenyl)-2-phenylethanone, (which is obtained by condensation of benzyl cyanide with ethyl p-methoxybenzoate).

sodium 4-(4-n-butoxybenzoyl) phenyl 3,5-dimethylphenyl phosphate from 4-hydroxy-4'-n-butoxy-benzophenone (which is obtained from Friedel-Craft reaction between 4-n-butoxybenzoyl chloride and phenol).

sodium 4(4-dimethylaminobenzoyl) phenyl 3,5-dimethylphenyl phosphate from 4-hydroxy-4'-dimethylamino-benzophenone.

In substantially the same manner the following compound is obtained starting from 3,5-dimethoxyphenyl phosphorodichloridate (which is obtained from 3,5-dimethoxy-phenol and phosphorus oxychloride) and monophenolic compound given below.

sodium 4-(4-methoxybenzoyl)-3-methoxyphenyl 3,5-dimethoxyphenyl phosphate from 4-hydroxy-2,4'-dimethoxybenzophenone (which is obtained from Friedel-Craft reaction between m-methoxyphenol and p-methoxybenzoyl chloride).

EXAMPLE 4

A solution of 2.42 g (0.01 mol) 3-(4-hydroxyphenyl)-2'-hydroxypropiophenone in 10 ml of pyridine is slowly added with stirring to a solution of 3.15 g (0.015 mol) phenylphosphorodichloridate in 40 ml of pyridine at a temperature of −40° C. After one hour at −20° C the temperature is kept at 0° C for one hour. The reaction mixture is poured on crushed ice and the resulting solution evaporated in vacuo. The residue solution is poured into a mixture of 5 M hydrochloric acid and crushed ice, and extracted with ethyl acetate. The ethyl acetate phase is washed with water and evaporated in vacuo. The residue oil is dissolved in ethanol and precipitated with water. The oil is neutralized to pH 5, evaporated in vacuo and refluxed with benzene. The precipitate formed is sodium 4-(3-(2-hydroxyphenyl)-3-oxopropyl)-phenyl phenyl phosphate, pure according to TLC.

EXAMPLE 5

5.9 g of 3-(4-diethylaminophenyl)-4'-hydroxypropiophenone is dissolved in 70 ml of dry pyridine, and this solution is slowly added (1 h) with stirring to a solution of 23.8 g phenylphosphorodichloridate in 100 ml dry pyridine at −10° C. After another hour at −10° C and one hour at room temperature the reaction mixture is poured on crushed ice. The next day the solution obtained is evaporated in vacuo to remove pyridine, water is added and the separated oil is mixed with water, pH is adjusted to 9 with 1 M sodium hydroxide and the solution is freeze-dried. The freeze-dried product is treated with acetone, and the undissolved is filtered. The clear acetone solution is evaporated in vacuo, the residue dissolved in water and freeze-dried.

Yield 3.1 g of
sodium 4-(3-(4-diethylaminophenyl)propionyl)phenyl phenyl phosphate In substantially the same manner is prepared
sodium 4-(3-(2-dimethylaminomethylphenyl)propionyl)phenyl phenyl phosphate from 3-(2-dimethylaminomethylphenyl)-4'-hydroxy-propiophenone.

EXAMPLE 6

40 g of 2',4',6'-tribenzoyloxy-3-(4-hydroxyphenyl) propiophenone (see Example 19) dissolved in 400 ml of pyridine is slowly (90 min) added with stirring to a solution of 100 g of phenyl phosphorodichloridate in 400 ml of dry pyridine at −10° C. After an hour at 0° C the reaction mixture is kept at room temperature until the next day. It is then poured on crushed ice (400 g) and evaporated in vacuo to a volume of about 300 ml. It is then poured in a mixture of 900 ml of conc. hydrochloric acid and 900 g of ice. The solution is decanted and the precipitate is dissolved in 350 ml of ethanol and reprecipitated by adding 700 ml of water. The dissolving in ethanol and precipitating with water is repeated once. The residue is dissolved in 1000 ml of ethyl acetate. The solution is dried with anhydrous sodium sulphate and evaporated to dryness in vacuo. The residue is dissolved in 670 ml of methanol and at a temperature of +20° C 200 ml of 2.5 M sodium hydroxide solution is added under nitrogen. After 30 min. at 20° C the pH-value is adjusted to 5.0 with 5 M hydrochloric acid and the mixture evaporated in vacuo to a volume of about 150 ml. An oil is obtained which is collected and treated with 4 × 400 ml ether to remove benzoic acid. The residue is then treated with 800 + 400 ml of ethyl acetate. The solution obtained is dried with sodium sulphate and evaporated in vacuo. The residue is dissolved in water so that a clear solution is obtained. By freeze-drying of this solution sodium 4-(3-oxo-3-(2,4,6-trihydroxyphenyl)propyl)phenyl phenyl phosphate is obtained as a yellow powder. The compound is pure in TLC and its structure is confirmed by NMR.

In substantially the same manner the following derivates are prepared:
sodium 4-(3-(2,4-dihydroxyphenyl)-3-oxopropyl)phenyl phenyl phosphate
sodium 4-(3-(3-hydroxyphenyl)-3-oxopropyl)-2-methoxy-phenyl 3-trifluoromethylphenyl phosphate.
sodium 4-(3-(3-hydroxyphenyl)-3-oxopropyl)-2-methoxyphenyl 3,5-dimethylphenyl phosphate
sodium 3,5-dimethylphenyl 4-(3-(2,4,6-trihydroxyphenyl)-3-oxo-propyl-oxo-propyl)phenyl phosphate.
sodium 4-(3-(4-hydroxyphenyl)-3-oxopropyl)phenyl phenyl phosphate
sodium 4-(3-(2,4-dihydroxyphenyl)-3-oxopropyl)phenyl 3,5-dimethyl phenyl phosphate These five phosphate esters are prepared from the appropriately substituted phenyl phosphorodichloridates and hydroxy-substituted 3-phenylpropiophenones having structures apparent from the end products and having all hydroxy groups except those to be phosphorylated protected by benzoate ester groups. Each of these propiophenones is prepared according to Example 3 from an acetophenone and a benzaldehyde both being substituted with the hydroxy and benzoyloxy groups necessary for the desired propiophenones, in reactions involving firs a condensation and then reduction of the double bond formed in the condensation.

In substantially the same manner the following secondary phosphoric acid esters are obtained.
sodium 4-(2-(4-hydroxyphenyl)hexanoyl)phenyl phenyl phosphate from 4'-acetoxy-α-butyl-4-hydroxy-deoxybenzoin (which is obtained by monoacetylation with aceticanhydride of α-butyl-4,4'-dihydroxydeoxybenzoin. The latter compound is obtained from 4,4'-dimethoxydeoxybenzoin by monoalkylation with n-butylbromid, followed by demethylation with pyridine hydrobromide).

sodium 4-(2-(4-hydroxyphenyl)-3-phenylpropionyl)phenyl phenyl phosphate from 4'-acetoxy-α-benzyl-4-hydroxydeoxybenzoin (which is obtained by monoacetylation with acetic anhydride of α-benzyl-4,4'-dihydroxydeoxybenzoin. The latter compound is obtained from 4,4'-dimethoxydeoxybenzoin by monobenzylation with benzyl bromide, followed by demethylation with pyridine hydrobromide).

sodium 3-hydroxy-4-(4-methoxyphenylacetyl)phenyl phenyl phosphate from 2-benzoyloxy-4-hydroxy-4'-methoxy-deoxybenzoin which is prepared from 2,4-dihydroxy-4'-methoxydeoxybenzoin through 2-hydroxy-4-methoxy-methoxy-4'-methoxydeoxybenzoin and 2-benzoyloxy-4-methoxy-methoxydeoxybenzoin sodium 3-hydroxy-4-(4-methoxyphenylacetyl)-2-methylphenyl phenyl phosphate from 2-benzoyloxy-4-hydroxy-4'-methoxy-3-methyldeoxybenzoin (which is obtained from 2,4-dihydroxy-4'-methoxy-3-methyldeoxybenzoin through 2-hydroxy-4-methoxymethoxy-4-methoxy-3-methyldeoxybenzoin and 2-benzoyloxy-4-methoxy-methoxy-4'-methoxy-3-methyldeoxybenzoin).

sodium 3-hydroxy-4-benzoylphenyl phenyl phenyl phosphate from 2-benzoyloxy-4-hydroxybenzophenone (which is obtained from 2,4-dihydroxy-benzophenone through 2-hydroxy-4-methoxy-methoxybenzophenone and 2-benzoyloxy-4-methoxymethoxy benzophenone).

sodium 4-(2-(4-hydroxyphenyl)-1-oxo-3-phenyl-2-propenyl)phenyl phenyl phosphate from 2-(4-benzoyloxyphenyl)-1-(4-hydroxyphenyl)-3-phenyl-2-propen-1-one (which is prepared from 1,2-bis(4-hydroxyphenyl)-3-phenyl-2-propen-1-one. The latter compound is obtained by condensation of 4,4'-dimethoxybenzoin and benzaldehyde and demethylation of the reaction product with pyridine hydrobromide).

sodium 4-(2-hydroxy-1-oxo-2-phenyl ethyl)phenyl 3,5-dimethylphenyl phosphate (which is obtained from 1-(4-hydroxyphenyl)-2-acetoxy-2-phenylethanone. The latter compound is obtained from 1-(4-hydroxyphenyl)-2-hydroxy-2-phenylethanone through 1-(4-methoxymethoxy phenyl)-2-hydroxy-2-phenylethanone and 1-(4-methoxymethoxyphenyl)-2-acetoxy-2-phenylethanone).

sodium 4-(2-(4-hydroxyphenyl)-4-penteoyl)phenyl phenyl phosphate (which is obtained from 4'-acetoxy-α-allyl-4-hydroxydeoxybenzoin. The latter compound is obtained by monoacetylation with acetic anhydride of α-allyl-4,4'-dihydroxydeoxybenzoin, which is obtained by monoalkylation of 4,4'-dimethoxy-deoxybenzoin, followed by demethylation with pyridine hydrobromide).

sodium 4-(2-(4-hydroxyphenyl)butyryl)phenyl phenyl phosphate from 4'-acetoxy-α-ethyl-4-hydroxydeoxybenzoin (which is obtained from α-ethyl-4,4'-dihydroxydeoxybenzoin by monoacetylation with acetic anhydride).

EXAMPLE 7

8 g of the 4',5-dibenzoate of naringenine (prepared by partial debenzoylation of the naringenine-4',5,7-tribenzoate according to a method described by L. Farkas et. al. in Chem. Ber. 102 (1969) 2583) is dissolved in 85 ml dry pyridine and slowly added (60 min) with stirring to a solution of 21.2 g of phenyl phosphorodichloridate in 85 ml dry pyridine at −10° C. After an hour at 0° the reaction mixture is kept at room temperature until the next day. It is then poured on crushed ice (85 g) and the remaining solution evaporated in vacuo to a volume of about 40 ml. This solution is poured into a mixture of 5 M hydrochloric acid (250 ml) and crushed ice (100 g). The precipitate obtained is collected by filtration, washed with water and then dissolved in ethanol (60 ml) and reprecipitated with water (150 ml). The dried precipitate is the 7-(phenyl hydrogen phosphate) of naringenine-4',5-dibenzoate. This compound is dissolved in 150 ml of methanol and 2,8 g of sodium hydroxide dissolved in 30 ml of water is added. After 10 min. pH of the solution is reduced to 2,5 by addition of 5 M hydrochloric acid. The solvents are evaporated at reduced pressure. The residue is extracted with ethyl acetate. The solution is collected and the solvent is evaporated under vacuum. The residue is washed with ether and then dissovled in 50 ml of 1 M sodium hydroxide. The solution is poured into 50 ml of 5 M hydrochloric acid. The mixture is extracted with ethyl acetate. The organic phase is washed with water and dried with magnesium sulphate. The solvent is evaporated and the residue is mixed with 100 ml of water and dissolved by addition of 1 M sodium hydroxide to pH 6. Freeze-drying of the solutin gives sodium 3,5-dihydroxy-4-(3-(4-hydroxyphenyl)acryloyl)phenyl phenyl phosphate which shows one spot in TLC and has a NMR-spectrum confirming its structure. This compound is then hydrogenated with 10% Pd/C as catalyst in ethanol to sodium 3,5-dihydroxy-4-(3-(4-hydroxyphenyl)propionyl)phenyl phenyl phosphate.

This hydrogenated compound is also obtained directly from the 7-(phenyl hydrogen phosphate) of naringenine-4',5-dibenzoate by hydrogenating this compound (2.2 g) dissolved in 0.5 M sodium hydroxide (80 ml) with 0.5 g 10% Pd/C as catalyst.

In substantially the same manner is prepared sodium 3,5-dimethylphenyl 3,5-dihydroxy-4-(3-(4-hydroxyphenyl)propionyl)phenyl phosphate by using 3,5-dimethylphenyl phosphorodichloridate instead of phenyl phosphorodichloridate, and sodium 4-(3-(4-hydroxyphenyl)-3-oxopropyl)phenyl phenyl phosphate from 3'-hydroxyflavone and phenyl phosphorodichloridate.

EXAMPLE 8

3.6 g of 4'-hydroxy-7-methoxymethoxyflavanone dissolved in 75 ml of pyridine is added with stirring over 30 min to a solution of 15.2 g of phenyl phosphorodichloridate in 75 ml of pyridine kept at −10° C. The mixture is allowed to stand for 1 hour at 0° C and over night at room temperature, and is then poured on 75 g of ice. After concentration by evaporation under vacuum to about 50 ml the solution is added to dilute hydrochloric acid. The unsoluble material is collected and mixed with water. 1 M sodium hydrogen carbonate solution is added until pH 5 was reached. The mixture is extracted with ethyl acetate and ether. The aqueous phase (125 ml) is mixed with 16 ml of 5 M sodium hydroxide and 300 mg of 10% Pd/C as catalyst and hydrogenated at room temperature and atmospheric pressure until the calculated amount of hydrogen is absorbed. The catalyst is removed and the solution is added to 2 M hydrochloric acid saturated with sodium chloride and extracted with ethyl acetate. The organic phase is evaporated, and the residue is refluxed for 5 min with a mixture of 100 ml of acetic acid, 20 ml of water and 1 ml of 2 M sulfuric acid. The mixture is cooled to room temperature, added to 2 M hydrochloric acid saturated with sodium chloride and extracted with ethyl acetate. The organic phase is washed with a saturated sodium chloride solution and added to water. pH is adjusted to 4.5 with 1 M sodium hydrogen carbonate. The aqueous phase is evaporated to remove dissolved ethyl acetate and freeze-dried. The solid material is dissolved in methanol. The solution is passed through a column containing Dowex 50W×8, 100–200 mesh, (H-form), concentrated and chromatographed on Sephadex LH 20 with methanol as eluant. The fraction containing the desired product is neutralized with 1 M sodium hydroxyde to pH 5. The methanol is evaporated at reduced pressure. The residue, which dissolved in water and freeze-dried, is sodium 4-(3-(2,4-dihydroxyphenyl)-3-oxopropyl)phenyl phenyl phosphate. The compound is pure in TLC and has a NMR-spectrum confirming its structure.

In a similar manner, starting with 3'-hydroxy-7-methoxymethoxyflavanone, the sodium 3-(3-(2,4-dihydroxyphenyl)-3-oxopropyl)phenyl phenyl phosphate is obtained. The two flavanones used for the phosphorylations are obtained from 2',4'-dihydroxyacetophenone which is transferred to 2'-hydroxy-4'-methoxymethoxyacetophenone and then condensed with 4-hydroxybenzaldehyde and 3-hydroxybenzaldehyde respectively substantially in the manner described in Ann.-Chim. (Rome) 48, 111 (1958).

EXAMPLE 9

3.6 of 2-chloromethyl-4-nitrophenyl p-tolyl hydrogen phosphate (Tetrahedron Letters. No. 40, p. 3505–3508, 1970) 5.9 of 4-hydroxy-2',4',6'-trimethoxybenzophenone and 4 ml of dry pyridine is kept at room temperature for two days and then heated at 90° C over night. 30 ml of absolute ethanol is added and the mixture is stirred at room temperature for several minutes. A yellow precipitate of 1(2'-hydroxy-5'-nitro-benzyl)-pyridinium chloride is filtered and washed with two 20 ml portions of absolute ethanol.

The combined alcoholic filtrate and washings are evaporated to dryness under reduced pressure. The residue is poured into a mixture of 25 ml of 2 M hydrochloric acid and ethyl acetate. Water is added to the organic layer and pH is adjusted to 5 with 1 M sodium hydroxide. The aqueous layer is freeze-dried giving sodium 4-methylphenyl 4-(2,4,6-trimethoxybenzoyl)-phenyl phosphate.

In substantially the same manner the following compound is obtained:
sodium4-methylphenyl 4(3-oxo-3-phenylpropyl)phenyl phosphate.

EXAMPLE 10

Hydrogen chloride is led for 6 hours with stirring into a solution of 3-(2-cyanoethyl)phenyl 3,5-dimethyl-phenyl hydrogen phosphate 72 g (0.238 mol) (prepared from 3-(2-cyanoethyl)phenol and 3,5-dimethylphenyl phosphrorodichloridate in substantially the same manner as in Example 3), phloroglucinol 30 g (0.238 mol), sulfolane 50 ml and zinc chloride 31.4 g. (0.238 mol) kept at 0° C. The mixture is kept at about 5° C over night, diluted with 150 ml of sulfolane and poured into 2 l of benzene with stirring which is continued for 20 min. The benzene solution is decanted and the oily residue is treated first with 1 l of benzene and then with 2 ÷ 1 l of diethyl ether. The oily residue is refluxed under nitrogen with 3 l of aq. and 2 l of methanol for 7 hours. The cooled solution is meutralized to pH 5 with 2 M sodium hydroxide. The methanol is evaporated in vacuo and the residue is mixed with 2 M HCl and extracted with ethyl acetate. The ethyl acetate solution is mixed with water and titrated with 1 M NaOH to pH 5. Diethylether is added. The aqeuos phase is collected and, after removing its opalescence with celite freeze-dried. The crude product is dissolved in methanol and put on a Dowex 50W×8 100–200 mesh (H-form) column. The crude secondary phosphate is eluated with methanol. The methanol solution is concentrated to 200 ml and chromoatographed on a 1 M Sephadex × LH 20 column which is eluated with methanol. The fraction containing 3-(3-(2,4,6-trihydroxyphenyl)-3-oxopropyl)phenyl phenyl hydrogen phosphate is titrated to pH 5 with 1 M sodium hydroxide. The methanol is evaporated at reduced pressure. The residue is dissolved in water and freeze-dried. The residue is sodium 3-(3-(2,4,6-trihydroxyphenyl)-3-oxopropyl)phenyl 3,5-dimethyl-phenyl phosphate showing one spot on TLC.

In substantially the same manner the following compounds are obtained.
sodium 4-(3-(2,4-dihydroxyphenyl)-3-oxopropyl)phenyl phenyl phosphate
sodium 3-(3-(2,4-dihydroxyphenyl)-3-oxopropyl)phenyl phenyl phosphate
sodium 4-(4-(2,4-dihydroxyphenyl)-4-oxobutyl)phenyl 3,5dimethylphenyl phosphate
sodium 3,5-dimethylphenyl 4-(4-oxo-4-(2,4,6-trihydroxyphenyl)-n-butyl)phenyl) phosphate
sodium 3,5-dimethylphenyl 4-(4-oxo-4-(2,4,6-trimethoxyphenyl)-n-butyl)phenyl) phosphate
sodium 4-(2-(2,4,6-trimethoxyphenyl)-2-oxethyl)phenyl phenyl phosphate
sodium 4-(2,4,6-trihydroxybenzoyl)phenyl phenyl phosphate
sodium 4-(2-oxo-2-(2,4,6-trihydroxyphenyl)ethyl)phenyl phenyl phosphate The starting materials for the above mentioned compounds are substituted or unsubstituted phenylphosphoryl chloridates, a cyano substituted phenol and a polyhydroxy or polymethoxy benzene with structures parent from the end products given above.

EXAMPLE 11

Acetic anhydride (5.1 g, 50 mmoles) is added to a solution of sodium 4-(3-oxo-3-(2,4,6-trihydroxyphenyl)-propyl)phenyl phenyl phosphate (Example 6) (4.5 g) in 20 ml of pyridine and triethylamine (1.02 g, 10 mmol). The mixture is kept at room temperature for 18 hours and poured on 200 g of ice-water. The pH of the mixture is adjusted to 1 with 1 M hydrochloric acid at 0° C. The aqueous phase is discarded. The residue is ground with ice-water and dissolved in acetone:aq., 1:3. The pH of the solution is adjusted to 5. The acetone is evaporated in vacuo and the remaining syrup precipitate which solidifies on standing is almost pure sodium 4-(3-oxo-3-(2,4,6-triacetoxyphenyl)-propyl)-phenyl phenyl phosphate. The structure is confirmed by NMR.

In substantially the same manner the following substances are prepared:
sodium 4-(2-(4-acetoxyphenyl) butyryl)phenyl phenyl phosphate from sodium 4-(2-(4-hydroxyphenyl)-butyryl)phenyl phenyl phosphate (Ex. 6)
sodium 4-(2-(4-acetoxyphenyl)hexanoyl)phenyl phenyl phosphate from sodium 4-(2-(4-hydroxyphenyl)hexanoyl)phenyl phenyl phosphate. (Ex. 6)

sodium 4-(2-(4-acetoxyphenyl)-3-phenyl-propionyl))-phenyl phenyl phosphate from sodium 4-(2-(4-hydroxyphenyl)-3-phenylpropionyl) phenyl phenyl phosphate. (Ex. 6)

sodium 3-acetoxy-4-(4-methoxyphenylacetyl)-2-methylphenyl phenyl phosphate from sodium 3-hydroxy-4-(4-methoxyphenylacetyl)-2-methylphenyl phenyl phosphate. (Ex. 6)

sodium 3-acetoxy-4-benzoylphenyl phenyl phosphate from sodium 3-hydroxy-4-benzoylphenyl phenyl phosphate. (Ex. 6)

sodium 4-benzoyl-2,6-dimethylphenyl 3-acetylaminophenyl phosphate from sodium 4-benzoyl-2,6-dimethylphenyl 3-aminophenyl phosphate, (Ex. 14)

sodium 4-(3-acetylaminobenzoyl)-phenyl 3,5-dimethylphenyl phosphate from sodium 4-(3-aminobenzoyl)-phenyl 3,5-dimethylphenyl phosphate (Ex. 14)

sodium 4-(2-(4-acetoxyphenyl)-4-phentoyl) phenyl phenyl phosphate from sodium 4-(2-(4-hydroxphenyl)-4-pentonoyl) phenyl phenyl phosphate. (Ex. 6)

sodium (2oxo-2-(2,4,6-triacetoxyphenyl ethyl)phenyl phenyl phosphate from sodium (2-oxo-2-(2,4,6-trihydroxyphenyl) ethyl)phenyl phenyl phosphate. (Ex. 10)

sodium 3-acetoxy-4-(4-methoxyphenylacetyl)phenyl phenyl phosphate from sodium 3-hydroxy-4-(4-methoxyphenylacetyl)phenyl phenyl phosphate (Ex. 6)

sodium 3-(2,4,6-trimethylbenzoyl)phenyl 4-acetoxyphenyl phosphate from sodium 3-(2,4,6-trimethylbenzoyl)phenyl 4-hydroxyphenyl phohsphate. (Ex. 16)

sodium 4-(2-(4-acetoxyphenyl)-1-oxo-3-phenyl-2-propenyl)phenyl phenyl phosphate from sodium 4-(2-(4-hydroxyphenyl)-1-oxo-3-phenyl-2-propenyl)phenyl phenyl phosphate. (Ex. 6)

sodium 4-(2-acetoxy-1-oxo-2-phenylethyl)phenyl 3,5-dimethylphenyl phosphate from sodium 4-(2-hydroxy-1-oxo-2-phenylethyl) phenyl 3,5,-dimethylphenyl phosphate. (Ex. 6)

sodium 4-(4-acetylaminobenzoyl) phenyl 3,5-dimethyl phenyl phosphate from sodium 4-(4-aminobenzoyl) phenyl 3,5-dimethyl phenyl phosphate. (Ex. 14).

In substantially the same manner the following compounds are obtained from compounds, which are prepared in Example 1 sodium 4-(3-(2,4,6-tripropionyloxyphenyl)-3-oxopropyl)phenyl phenyl phosphate.

sodium 3,5-dimethylphenyl 3-(3-(2,4,6-triacetoxyphenyl)-3-oxopropyl)phenyl phosphate.

sodium 3,5-dimethylphenyl 3-(3-(2,4,6-tripropionyloxyphenyl)-3-oxopropyl)phenyl phosphate.

sodium 2-methoxy-4-(3-(3-pivaloyloxyphenyl)-3-oxopropyl)phenyl 3-trifluoromethylphenyl phosphate.

sodium 4-(3-(3-acetamidophenyl)-3-oxopropyl)phenyl phenyl phosphate.

sodium 4-(4-(2,4-dipropionyloxyphenyl)-4-oxobutyl)phenyl 3,5-dimethylphenyl phosphate.

sodium 3,5-dimethylphenyl 4-(3-(2,4,6-triacetoxyphenyl)-3-oxopropyl)phenyl phosphate.

sodium ethyl 4-(3-oxo-3(2,4,6-triacetoxyphenyl)propyl) phenyl phosphate.

sodium 3,5-dimethylphenyl 4-(3-(2,4,6-tripropionyloxyphenyl)-3-oxopropyl)phenyl phosphate.

sodium 3-acetamidophenyl 4-(3-oxo-3-phenylpropyl)phenyl phosphate.

sodium 4-acetoxyphenyl 4-(3-oxo-3-phenylpropyl)phenyl phosphate.

sodium phenyl 4-(3-(2,4-dipropionyloxyphenyl)-3-oxopropyl)-phenyl phosphate.

sodium 3-(3-(2,4-diacetoxyphenyl)-3-oxopropyl)phenyl phenyl phosphate.

sodium 3,5-dimethylphenyl 4-(4-(2,4,6,-triacetoxyphenyl)-n-butyl)phenyl phosphate

EXAMPLE 12

5 g of sodium 3-(2,4,6-trimethylbenzoyl)phenyl 4-hydroxyphenyl phosphate (Ex. 16) is dissolved in 50 ml dry pyridine and the solution added to a solution of 8.5 g phosphoros oxychloride in 80 ml dry pyridine. The temperature is maintained at $-5°$ C during the addition. After the addition the mixture is kept at 0° C for one hour and at room temperature for one hour. The solution is then poured in a mixture of 100 ml water and 200 g ice. Afteer evaporation to about 200 ml of the solution is poured into a mixture of 100 ml hydrochloric acid and 200 g of ice. The precipitate is filtered off and washed with cold water. The residue is dissolved in water with 2N sodium hydroxide to a pH-value of about 5 and the solution freeze-dried. The disodium salt of 3-(2,4,6-trimethylbenzoyl)phenyl 4-dihydroxyphosphinyloxyphenyl hydrogen phosphate is obtained.

In substantially the same manner the following compounds are obtained.

disodium salt of 4-(-dihydroxyphosphinyloxyphenyl)-1-oxo-3-phenyl-2-propenyl)phenyl phenyl hydrogen phosphate from sodium 4-(2-(4-hydroxyphenyl)-1-oxo-3-phenyl-2-propenyl)-phenyl phenyl phosphate (Ex. 6)

disodium salt of 4-dihydroxphosphinyloxphenyl 4-(3-oxo-3-phenylpropyl)phenyl hydrogen phosphate from sodium 4-hyroxyphenyl 4(3-oxo-3-phenylpropyl)phenyl phosphate

EXAMPLE 13

To a mixture of 22.5 g sodium 4-(3-(3-hydroxyphenyl)-3-oxopropyl)-2-methoxyphenyl 3,5-dimethylphenyl phosphate (see Example 6) and 1000 ml of 0.22 M sodium ethoxide kept under nitrogen, 5.7 g of chloroacetic acid in 50 ml anhydrous ethanol is added dropwise with stirring and the mixture being kept boiling. After all of the acid is added the refluxing is continued for one hour. The reaction mixture is cooled and sodium chloride is removed by filtration. The solvent is evaporated under vacuum, and the residue is dissolved in water, acidified with 2 M hydrochloric acid and extracted with ethyl acetate. The organic layer is washed with saturated sodium sulphate solution. Water is added and pH adjusted to 7 with 2 M sodium hydroxide. The water layer is freeze-dried giving disodium 4-(3-(3-carboxylatomethoxyphenyl)-3-oxopropyl)-2-methoxyphenyl 3,5-dimethylphenyl phosphate.

EXAMPLE 14

4.25 g. of sodium 4-(3-(3-nitrophenyl)-3-oxopropenyl) phenyl phenyl phosphate (see Example 3) is 500 ml 0.02 M sodium hydroxide in methanol/water (1:1) at room temperature and atmospheric pressure with 0.3 g of 10% Pd/C as catalyst. The reaction almost stops when the calculated amounts of hydrogen has been absorbed. The catalyst is removed by filtration and the solvent is evaporated. The residue is dissolved in water and freeze-dried giving sodium 4-(3-(3-aminophenyl)-3-oxopropyl)phenyl phenyl phosphate In substantially the same manner
sodium 3-aminophenyl 4-(3-oxo-3-phenylpropyl)phenyl phosphate
sodium 4-aminophenyl 4-(3-phenyl-3-oxopropyl)phenyl phosphate
sodium 2-aminophenyl 4-(3-phenyl-3-oxopropyl)phenyl phosphate are obtained from the corresponding nitro compounds prepared in Example 3.

In substantially the same manner the following compounds are obtained.
sodium 4-(4-aminobenzoyl)phenyl 3,5-dimethyl phenyl phosphate from sodium 4-(4-nitrobenzoyl)phenyl phenyl phosphate (Ex. 3)
sodium 4-benzoyl-2,6-dimethylphenyl 3-aminophenyl phosphate from sodium 4-benzoyl-2,6-dimethylphenyl 3-nitrophenyl phoshate (Ex. 3).
sodium 4-(3-aminobenzoyl)phenyl 3,5-dimethyl phenyl phosphate from sodium 4-(3-nitrobenzoyl)phenyl 3,5-dimethyl phenyl phosphate (Ex. 3).

EXAMPLE 15

5 g of 4-(2-methoxycarbonylbenzoyl)phenyl phenyl hydrogen phosphate is dissolved in 250 ml ethanol. To the solution is slowly added 100 ml 1 M sodium hydroxide solution and the mixture is allowed to stand at room temperature over night. The pH is then adjusted to near neutral with hydrochloric acid, whereupon the solution is evaporated to as small a volume as possible without any precipitation. This solution is poured into 5 M hydrochloric acid (150 ml). The precipitate is collected, dissolved in aqueous sodium hydroxide and reprecipitated with hydrochloric acid. The substance so obtained is pure in TLC. The substance is dissolved in acetone:water (1:4) with sodium hydroxide to a pH-value of about 4. Most of the acetone is removed in vacuo and the remaining water solution freeze-dried.

The salt obtained is sodium 4-(2-carboxybenzoyl)-phenyl phenyl phosphate.

In substantially the same manner the following compounds are obtained.
sodium 4-benzoyl-3-carboxyphenyl 3,5-dimethylphenyl phosphate from 4-benzoyl-3-methoxycarbonylphenyl 3,5-dimethylphenyl hydrogen phosphate.
sodium 2-benzoyl-4-carboxyphenyl phenyl phosphate from 2-benzoyl-4-methoxycarbonylphenyl phenyl hydrogen phosphate.
sodium -4-benzoyl-3-carboxy-methylphenyl 3,5-dimethylphenyl phosphate from 4-benzoyl-3-methoxycarbonylmethylphenyl 3,5-dimethylphenyl hydrogen phosphate.
sodium 2-benzoyl-4-carboxyl-methylphenyl 3,5-dimethylphenyl phoshate from 2-benzoyl-4-methoxycarbonylmethylphenyl 3,5-dimethylphenyl hydrogen phosphate.
sodium 4-benzoyl-3-carboxy-methoxyphenyl 3,5-dimethylphenyl phosphate from 4-benzoyl-3methoxycarbonylmethoxyphenyl 3,5-dimethylphenyl hydrogen phosphate.
sodium 3-benzoyl-4-carboxymethoxyphenyl phenyl phosphate from 3-benzoyl-4-methoxycarbonylmethoxyphenyl phenyl hydrogen phosphate.
sodium 2-benzoyl-4-carboxymethoxyphenyl phenyl phosphate from 2-benzoyl-4-methoxycarbonylmethoxyphenyl phenyl hydrogen phosphate.
sodium 4-(2-carboxybenzoyl)phenyl 3,5-dimethylphenyl phosphate from 4-(2-methoxycanbonylbenzoyl)-phenyl 3,5-dimethyl phenyl hydrogen phosphate.

EXAMPLE 16

2.86 g 3-hydroxy-2',4',6'-trimethylbenzophenone (which is obtained from Friedel-Craft reaction between mesitylene and m-metoxybenzoyl chloride, followed by demethylation with pyridine hydrobromide) is dissolved in 50 ml dry pyridine and the solution slowly added to a solution of 34.4 g phenyl-1,4-bis(phosphodichloridate) in 500 ml dry pyridine. The temperature is maintained at −50° C during the addition. The solution is then kept at 0° C for 2 hours and at room temperaure for 1 hour. The solution is poured on 300 g ice and kept in a refrigerator over night. After evaporation in vacuo to a volume of about 100 ml, 33 ml 10 M sodium hydroxide solution and 50 ml acetate buffer (0.4 M, pH 5) is added and the solution is refluxed for 20 hours. The solution is cooled, acidified with hydrochloric acid and extracted with ethyl acetate. The solution is dried over anhydrous sodium sulphate, filtered and evaporated to dryness. The residue is purified by column chromatography. The fraction containing the desired substance, as checked with TLC, is collected and the solvent evaporated, giving the desired compound as an oil. The substance is dissolved in acetone:water with sodium hydroxide to a pH-value of about 4. Most of the acetone is removed in vacuo and the remaining water solution freeze-dried.

The salt obtained is sodium 3-(2,4,6-trimethylbenzoyl) phenyl 4-hydroxyphenyl phosphate.

In substantially the same manner the following compound is prepared:
4-hydroxphenyl 4-(3-oxo-3-phenylpropyl)phenyl hydrogen phosphate.

EXAMPLE 17

5 g of 3-(2,4,6-trimethylbenzoyl)phenyl 4-methoxycarbonylphenyl hydrogen phosphate is suspended in 100 ml 10 M ammonia and the mixture stirred at room temperature for 24 hours. The mixture is carefully acidified with acetic acid and the precipitate filtered off and washed with water. The substance is dissolved in acetone:water with sodium hydroxide to a pH-value of about 4. Most of the acetone is removed in vacuo and the remaining water solution freeze-dried.

The salt obtained is sodium 3-(2,4,6-trimethylbenzoyl) phenyl 4-carbamoylphenyl phosphate.

In substantially the same manner the following compounds are obtained from compounds prepared in Example 3.
sodium 4-(2-carbamoylbenzoyl)phenyl 3,5-dimethylphenyl phosphate from 4-(2-methoxycarbonylbenzoyl)phenyl 3,5-dimethylphenyl hydrogen phosphate and ammonia.
sodium 4-benzoyl-3-carbamoylphenyl 3,5-dimethylphenyl phosphate from 4-benzoyl-3methoxycarbonylphenyl 3,5-dimethylphenyl hydrogen phosphate and ammonia.

sodium 4-benzoyl-3-carbamoylmethylphenyl 3,5-dimethylphenyl phosphate from 4-benzoyl-3-methoxycarbonylmethylphenyl 3,5-dimethylphenyl hydrogen phosphate and ammonia.

sodium 4-benzoyl-3-carbamoylmethoxyphenyl 3,5-dimethylphenyl phosphate from 4-benzoyl-3-methoxycarbonylmethoxyphenyl 3,5-dimethylphenyl hydrogen phosphate and ammonia.

EXAMPLE 18

2 g of sodium 3,5-dimethylphenyl 4(3-oxo-3-phenylpropyl) phenyl phosphate is dissolved in 150 ml water and 5 m 50% solution of calciumchloride in water is added. The precipitate formed is collected by filtration, washed with water and dried in vacuo. The product obtained is the calcium salt of 3,5-dimethylphenyl 4-(3-oxo-3-phenylpropyl)phenyl hydrogen phosphate.

EXAMPLE 19

2',4',6'-tribenzoyloxyacetophonone (83.5 g) and 4-hydroxybenzaldehyde are dissolved in 850 ml of ethyl acetate. Hydrogen chloride is led in at a temperature of 0° for 6 hours. The reaction mixture is then kept at about 5° for 4 days and then freed from most of the hydrogen chloride with nitrogen passed through the solution. The ethyl acetate is evaporated and the residue mixed with 300 ml benzene and evaporated to remove the remaining hydrogen chloride. The residue is mixed with abs. ethanol (460 ml). A crystalline solid is formed, collected by filtration and then suspended in ether and refluxed with stirring for 2 hours. After cooling, filtration and washing with ether there is obtained 41 g of 4-hydroxy-2',4',6'-tribenzoyloxy-chalcone with m.p. 198°-200°. This compound is dissolved in 1400 ml dioxane and hydrogenated at room temperature and atmospheric pressure with 4 g of 10% Pd/C as catalyst. When the theoretical amount of hydrogen has been absorbed the reaction is stopped, the catalyst removed by filtration and the dioxane evaporated in vacuo. The residue is recrystallized twice from abs. ethanol and 28 g of 3-(4-hydroxyphenyl)-2',4',6'-tribenzoyloxypropiophenone is obtained with a m.p. of 156°-8°.

EXAMPLE 20

25 g of 2',4',6'-tribenzoyloxy-3-(4-hydroxyphenyl) propiophenone (preparation see Example 19) is dissolved in 215 ml of dry pyridine and this solution is slowly added (1 hr) with stirring to a solution of 27 ml of phosphorur oxy-chloride in 250 ml of dry pyridine at −10° C. After another hour at −10° C and one hour at room temperature the reaction mixture is poured on crushed ice (500 g). Next day the solution obtained is evaporated in vacuo and the residue dissolved in a mixture of 200 ml of ethyl acetate and 200 ml of 2,5-M hydrochloric acid. The organic phase is collected and the aqueous phase is extracted once more with ethyl acetate. The combined organic phases are washed twice with wate and then dried with magnesium sulphate. The solvent is removed in vacuo and 4-(3-oxo-3-(2,4,6-tribenzoyloxyphenyl)propyl)phenyl dihydrogen phosphate is obtained as a yellow glass.

In substantially the same manner the following primary phosphoric acid esters are prepared:

4-(4-methoxybenzoyl)-3-5-dimethoxyphenyl dihydrogen phosphate from 4-hydroxy-2,4,6-trimethoxybenzophenone (which is obtained from Houben-Hoesch reaction between p-methoxybenzonitrile and 3,5-dimethoxyphenol).

4-benzoyl-2,6-dimethylphonyl dihydrogen phosphate from 4-hydroxy-3,5-dimetylbenzohphenone.

4-(2,4,6-trimethoxybenzoyl)phenyl dihydrogen phosphate from 4-hydroxy-2',4',6'-trimethoxybenzophenone.

4-(3-oxo-3-phenylpropyl)-phenyl dihydrogen phosphate from 3-(4-hydroxphenyl)propiophenone.

EXAMPLE 21

The PG-inhibitory effect of esters of the present invention on the gerbil colon are determined using the general technique described by Eakins, Miller & Karim (J. Pharm. Exp. Ther. 176:441, 1971). Gerbils (Meriones unguiculatus) of own breed, both sexes, weighing 50-80 g are used. The animal is stunned, colon ascendens immediately removed, and a 2-3 cm piece mounted in a 6 ml bath containing a modified de Jalon solution at 28° C and continuously oxygenated. Contractions of the organ are registered either isotonically or isometrically. When testing the inhibitory effect of a compound this is added to the bath 2 min. before the addition of prostaglandin. The antagonist (esters of this invention) is usually dissolved in saline, but occasionally an organic solvent such as ethanol has to be included. Several concentrations of each antagonist are used. In this system prostaglandins $E_1$, $E_2$, $F_{1\alpha}$ and $F_{2\alpha}$ produce suitable contractions of the organ in the concentration range 1-50 ng/ml.

Results from these experiments give an approximation of the PG-inhibitory potency of the compounds. When more precise information about this is desired we use a more elaborate method involving the establishment of several PR dose-response curves in the presence of various concentrations of inhibitor. The method used is essentially the same as that described by Arunlakshana & Schild (Br. J. Pharm. 14:48, 1959). Other agonists, acetylcholine, 5-HT and bradykinin, are included in these experiments in order to determine the selectivity of the antagonism.

Esters of the present invention cause a dose-dependent inhibition of the responses of the gut preparation to either of the prostaglandins tested. The concentration of polyphloretin phosphate (PPP) required to produce a 50 percent reduction of the PG-induced contraction is 10-75 μg/ml, the antagonist-agonist ratio being in the order of 2000-4000. The corresponding concentration of sodium 3,5-dimethylphenyl 4-(3-(2,4,6-trihydroxyphenyl)-3-oxopropyl)phenyl phosphate is only about one tenth of that of PPP.

The sodium salt of diphenyl phosphate is without effect in concentrations 10 times as high as that of PPP.

In addition the results with other agonists than prostaglandins show that the antagonism is very selective, far higher concentrations than the prostaglandin-inhibitory ones having no influence on the contractions elicited by acetylcholine, 5-HT or bradykinin.

The selective inhibitory effects of the following compounds are found to be equal to or superior to that of PPP.

sodium 4-(2,4,6-trimethoxybenzoyl)phenyl phenyl phosphate sodium 4-(2,4,6-trimethoxybenzoyl)phenyl propyl phosphate sodium 3-(2,4,6-trimethoxybenzoyl)phenyl phenyl phosphate sodium 3,5-dimethoxy-4-(4-methoxybenzoyl) 3,5-dimethylphenyl phosphate
sodium 4-(2-(2,4,6-trimethoxyphenyl)-2-oxoethyl)phenyl 3,5-dimethylphenyl phosphate
sodium 4-(2-(4-hydroxyphenyl)butyryl)phenyl phenyl phosphate
sodium 4-(2-(4-hydroxyphenyl)-3-phenylpropionyl)phenyl phenyl phosphate
sodium 4-(2-oxo-2-(2,4,6-trihydroxyphenyl)ethyl)phenyl phenyl phosphate
sodium 4-(2-carbamoylbenzoyl)phenyl 3,5-dimethylphenyl phosphate
sodium 4-benzoyl-3-carbamoylmethoxyphenyl 3,5-dimethylphenyl phosphate
sodium 4-(2-cyclohexyl-1-oxo-2-phenylethyl)phenyl phenyl phosphate
sodium 3-(2,4,6-trimethylbenzoyl)phenyl 4-fluorophenyl phosphate
disodium salt of 4-(2-(4-dihydroxyphosphinyloxyphenyl)-1-oxo-3-phenyl-2-propenyl)phenyl phenyl hydrogen phosphate
sodium 4-benzoyl-2,6-dimethylphenyl 3,5-dimethylphenyl phosphate
sodium 4-benzoyl-2,6-dimethylphenyl 3-acetylaminophenyl phosphate
sodium 4-benzoyl-2-propionylphenyl phenyl phosphate
sodium 2-(2,4-dimethylbenzoyl)phenyl phenyl phosphate
sodium 4-(4-trifluoromethylbenzoyl)phenyl 3,5-dimethylphenyl phosphate
sodium 4-(2-cyano-1-oxo-2-phenylethyl) phenyl 3,5-dimethyl phenyl phosphate
sodium 4-(2-(4-hydroxyphenyl)-4-pentenoyl) phenyl phenyl phosphate
sodium 4-(2-acetoxy-1-oxo-2-phenylethyl)phenyl 3,5-dimethylphenyl phosphate
sodium 4-(2-hydroxy-1-oxo-2-phenylethyl) phenyl 3,5-dimethylphenyl phosphate
sodium 4-(2,4,6-trimethoxybenzoyl)phenyl n-octyl phosphate
sodium 4-(2,4,6-trihydroxybenzoyl)phenyl phenyl phosphate
sodium 3-(3-(2,4-dihydroxyphenyl)-3-oxopropyl)phenyl phenyl phosphate
sodium 3,5-dihydroxy-4-(3-(4-hydroxyphenyl)acryloyl)phenyl phenyl phosphate
sodium ethyl 4-(3-oxo-3-(2,4,6-trihydroxyphenyl)propyl)phenyl phosphate
sodium ethyl 4-(3-oxo-3-(2,4,6-triacetoxyphenyl)propyl)phenyl phosphate
sodium cyclohexyl 4-(3-oxo-3-(2,4,6-trihydroxyphenyl)propyl) phenyl phosphate
sodium 3,5-dihydroxy-4-(3-(4-hydroxyphenyl)propionyl)phenyl phenyl phosphate
sodium phenyl 4-(3-oxo-3-(2,4,6-trimethoxyphenyl)propyl) phenyl phosphate
sodium 3,5-dimethoxy-4-(3-(4-methoxyphenyl)propionyl)phenyl 3,5-dimethylphenyl phosphate
sodium 3-hydroxy-4-(4-phenylbutyryl)phenyl 3,5-dimethoxyphenyl phosphate
sodium 4-(3-oxo-3-(2,4,6-trihydroxyphenyl)propyl)phenyl phenyl phosphate
sodium 4-(2-butyl)phenyl 4-(3-oxo-3-phenylpropyl)phenyl phosphate
sodium 3,5-dimethylphenyl 4-(3-oxo-3-phenylpropyl)phenyl phosphate
sodium 3-nitrophenyl 4-(3-oxo-3-phenylpropyl)phenyl phosphate
sodium 3-aminophenyl 4-(3-oxo-3-phenylpropyl)phenyl phosphate
sodium 4-hydroxyphenyl 4-(3-oxo-3-phenylpropyl)phenyl phosphate sodium 4-(3-oxo-3-phenylpropyl)phenyl 4-biphenylyl phosphate
sodium 2-naphthyl 4-(3-oxo-3-phenylpropyl)phenyl phosphate
sodium 3,5-dimethylphenyl 2-(3-phenylacryloyl)phenyl phosphate
sodium 3,5-dimethylphenyl 4-(3-(2,4,6-triacetoxyphenyl)-3-oxopropyl)phenyl phosphate
sodium 3-(3-(2,4,6-trihydroxyphenyl)-3-oxopropyl)phenyl 3,5-dimethyl-phenyl phosphate
sodium 4-(3-(3-hydroxyphenyl)-3-oxopropyl)2-methoxy-phenyl 3-trifluoromethylphenyl phosphate
sodium 2-methoxy-4-(3-(3-pivaloyloxyphenyl)-3-oxopropyl)phenyl 3-trifluoromethylphenyl phosphate
disodium 4-(3-(3-carboxylatomethoxyphenyl)-3-oxopropyl)-2-methoxyphenyl 3,5-dimethylphenyl phosphate
sodium 3,5-dimethoxyphenyl 2-methoxy-4-(3-trifluoromethylphenyl)-3-oxopropyl)phenyl phosphate
sodium 4-(3-(3-acetamidophenyl)-3-oxopropyl)phenyl phenyl phosphate
sodium 3-(3-(4-cyanophenyl)acryloyl)phenyl 3-ethyl-5-methylphenyl phosphate
sodium 4-(2-benzyl-n-hexanoyl)phenyl phenyl phosphate
sodium 4-(3-(4-carboxyphenyl)-2-(4-methoxyphenyl)acryloyl)-3-methoxyphenyl phenyl phosphate
sodium 4-(3-(2,4-dihydroxyphenyl)-3-oxopropyl)phenyl 3,5-dimethyl phenyl phosphate
sodium 4-(3-(4-diethylaminophenyl)propionyl)phenyl phenyl phosphate
sodium 4-(3-(4-fluorophenyl)-3-oxopropyl)phenyl phenyl phosphate
sodium 4-(3-(4-ethoxycarbonylmethyl-phenyl)3-oxopropyl)phenyl phenyl phosphate
sodium 4-(3-(4-N,N-dimethylcarbamoylmethylphenyl)-3-oxopropyl)phenyl 3,5-dimethylphenyl phosphate
sodium 4-(3-(2-dimethylaminomethylphenyl)propionyl)phenyl phenyl phosphate
sodium 3,5-dimethylphenyl 4-(4-oxo-4-(2,4,6-trihydroxyphenyl)-n-butyl)phenyl) phosphate
sodium 3,5-dimethylphenyl 4-(4-oxo-4-(2,4,6-trimethoxyphenyl)-n-butyl)phenyl) phosphate
sodium n-hexyl 4-(3-oxo-3-(2,4,6-trihydroxyphenyl)propyl)phenyl phosphate
sodium 3-(2-benzoyl-3-phenylpropyl)phenyl phenyl phosphate This example shows that the new compounds have utility as antagonists of various prostaglandins and also have the valuable property to exert these effects with selectivity.

EXAMPLE 22

The inhibitory effect of esters of the present invention has been investigated on the prostaglandin-stimulated corticosterone production by adrenals from male rats in vitro. The experiments were performed using adult Sprague-Dawley male rats weighing 200–250 g, which were housed 1 per cage under conditions of controlled lighting and temperature. Animal quarters were not entered during the 18 h preceding the experiment. The animals were sacrified by decapitation at 10 AM under conditions chosen to minimize disturbance of the animals. The adrenals were decapsulated and quartered and 8 adrenal quarters from different animals were distributed to 10 ml Erlenmeyer flasks containing 0.5 ml 0.9% saline and 2.0 ml Krebs-Ringer bicarbonate buffer, pH 7.4. The weight of the adrenal tissue in each flask was determined. The flasks were gassed with 95% $O_2$ – 5% $CO_2$ and preincubated at 37° C for 1 h with continuous shaking. Following preincubation the media were decanted and discarded. One ml of Krebs-Ringer buffer, with or without the additions of prostaglandin $E_2$ ($PGE_2$) sodium 3,5-dimethylphenyl 4-(3-(2,4,6-trihydroxyphenyl)-3-oxopropyl)phenyl phosphate.

(for details see below) was added to the flasks, which were then gassed with 95% $O_2$ – 5% $CO_2$ and kept at 37° C for 1 h. with continuous shaking. Following incubation, corticosterone levels were determined on 0.5 ml aliquots of the medium by the sulphuric acid fluorescence method.

In the first experiment (I) $PGE_2$ in a concentration of 1 μg/ml was added to the incubation medium containing the quartered adrenals. The result is shown in the Table and it can be seen that a highly significant increase in the corticosterone concentration is produced by $PGE_2$.

In the next experiment (II) different amounts of Leo 1258 to the incubation medium. The results reveal that when 0.25 and 1.0 mg of Leo 1258 were added to the incubation bath dose-related inhibition of the $PGE_2$-stimulated corticosterone production was seen.

flasks containing compounds of this invention dissolved in Krebs bicarbonate buffer. After that the ovaries have been preincubated during 60 min. at 37° C in this medium, they are blotted on filter paper and then washed for 2 min. in plain buffer. The ovaries are then transferred to a new incubation medium containing prostaglandins (PG) dissolved in Krebs bicarbonate buffer and incubated at 37° C for 2 hours with continuous shaking. The ovarian glycolysis is then determined by measuring the concentration of lactic acid in the incubation medium. When polyphloretin phosphate (PPP) is present in the preincubation medium in a concentration of 500 μg/ml, the subsequent ovarian lactic acid production produced by $PGE_1$ is reduced to about 50% of that obtained with ovaries preincubated in plain buffer.

When sodium 3,5-dimethylphenyl 4-(3-(2,4,6-trihydroxyphenyl)-3-oxo-propyl)phenyl phosphate is investigated in the same experimental system, a 50% reduction of the lactate production is seen, when only 50–100 μg/ml of the compound is present in the preincubation medium. Thus, this compound is 5–10 times more active as a prostaglandin inhibitor than PPP in the present experimental system.

Prostaglandin-inhibiting activity of the same order is also seen when the following compounds are tested:
sodium ethyl 4-(3-oxo-3-(2,4,6-trihydroxyphenyl)-propyl)phenyl phosphate Table

| Exp. no. | Group no. | Additions to incubation media | No. of observ. | Corticosterone production μg/100 mgx 1 h * | P |
|---|---|---|---|---|---|
| I | | Control | 4 | 3.4±0.2 | <0.001 |
| | | $PGE_2$ - 1 μg/ml | 4 | 7.6±0.4 | |
| II | A | Leo 1258 - 250 μg/ml | 4 | 3.9±0.5 | |
| | B | $PGE_2$ - 1 μg/ml | 4 | 8.4±0.5 | A/B <0.001 |
| | C | $PGE_2$ - 1 μg/ml Leo 1258-250 μg/ml | 4 | 6.5±0.5 | B/C <0.05 |
| | D | $PGE_2$ - 1 μg/ml Leo 1258 - 1 mg/ml | 4 | 2.9±0.2 | B/D <0.001 |

*) Mean ± standard error

Prostaglandin inhibiting activity of the same order is also seen when the following compounds are tested:
sodium ethyl 4-(3-oxo-3-(2,4,6-trihydroxyphenyl)-propyl)phenyl phosphate
sodium 3,5-dihydroxy-4-(3-(4-hydroxyphenyl)acryloyl)phenyl phenyl phosphate
sodium 3,5-dihydroxy-4-(3-(4-hydroxyphenyl)propionyl)phenyl phenyl phosphate
sodium 4-(3-oxo-3-(2,4,6-trihydroxyphenyl)propyl)phenyl phenyl phosphate
sodium 3-(3-(2,4,6-trihydroxyphenyl)-3-oxopropyl)phenyl 3,5-dimethyl-phenyl phosphate
sodium 4-(2-oxo-2-(2,4,6-trihydroxyphenyl)ethyl)phenyl phenyl phosphate
sodium 4-(2,4,6-trihydroxybenzoyl)phenyl phenyl phosphate This example shows that the new compounds are useful to prevent the corticosteroid production in adrenals caused by prostaglandins.

EXAMPLE 23

The action of esters of the present invention on the prostaglandin-stimulated glycolysis of the prepubertal ovary is investigated. The method used has been described in detail by Perkley & Ahren (Life Sciences Part I, 10:1387, 1971). In these experiments ovaries from prepubertal rats are removed and placed in Erlenmeyer sodium 3,5-dihydroxy-4-(3-(4-hydroxyphenyl)acryloyl)phenyl phenyl phosphate
sodium 3,5-dihydroxy-4-(3-(4-hydroxyphenyl)propionyl)phenyl phenyl phosphate
sodium 4-(3-oxo-3-(2,4,6-trihydroxyphenyl)propyl)phenyl phenyl phosphate
sodium 3-(3-(2,4,6-trihydroxyphenyl)-3-oxopropyl)phenyl 3,5-dimethyl-phenyl phosphate
sodium 4-(2-oxo-2-(2,4,6-trihydroxyphenyl)ethyl)phenyl phenyl phosphate
sodium 4-(2,4,6-trihydroxybenzoyl)phenyl phenyl phosphate This example shows that the new compounds are useful to antagonize the effect of prostaglandins on the ovary, which is of importance for the regulation of the hormone secretion from this organ (Behrman, H.R. et al. Am. J. Physiol. 221 (1971) 189).

EXAMPLE 24

The in vivo action of esters of the present invention on the prostaglandin-stimulated glycolysis of the prepubertal ovary is investigated in the following way:

Prepubertal rats, 24–26 days old, of the Sprague-Dawley strain, are injected intraperitoneally (i.p.) with 1 ml saline containing 500 μg sodium 3,5-dimethylphenyl 4-(3-(2,4,6-trihydroxyphenyl)-3-oxo-propyl)phenyl phosphate.

One hour later the animals are sacrificed by cervical fracture and the ovaries are removed and trimmed free of extraneous tissue. The ovaries are then transferred to an incubation bath containing prostaglandin $E_1$ ($PGE_1$; 0.4 μg/ml) dissolved in Krebs bicarbonate buffer and incubated at 37° C for 2 hours with continuous shaking. The ovarian glycolysis is then determined by measuring the concentration of lactic acid in the incubation medium. The details of the method have been described previously (Perklov, T & Ahren, K., Life Sciences Part I, 10:1387, 1971). In ovaries of animals treated with the phosphoric acid ester mentioned above, the glycolysis is significantly reduced compared to that measured in ovaries injected with saline. The same reduction in ovarian glycolysis is also seen when the following compounds are injected i.p. before the exposure of the ovaries to $PGE_1$ as described above:

sodium 3,5-dihydroxy-4-(3-(4-hydroxyphenyl)propionyl)phenyl phenyl phosphate sodium 4-(3-oxo-3-(2,4,6-trihydroxyphenyl)propyl)phenyl phenyl phosphate sodium 4-(2-oxo-2(2,4,6-trihydroxyphenyl)ethyl)phenyl phenyl phosphate This example shows that the new compounds exert the same effect as shown in the previous experiment also when they are injected into the animals.

EXAMPLE 25

The antagonism to Slow Reacting Substance (SRS) is determined on the isolated guinea-pig ileum as described by Mathe & Strandberg (Acta physiol. scand. 82:460, 1971). Purified SRS is obtained from cat paws perfused with compound 48/80 (Strandberg & Uvnas: Acta physiol. scand. 82:358, 1971). Sodium 4-(3-oxo-3-(2,4,6-trihydroxyphenyl)propyl)phenyl phenyl phosphate was tested in this system in several concentrations.

In concentrations as low as 5 μg/ml, it inhibits contractions produced by SRS, but not by histamine and bradykinin, in a competitive manner, i.e. parallel shift of the dose-response curves and with no change in maximum contraction.

The sodium salt of diphenyl phosphate is found to be without effect.

The following compounds of this invention are also found to inhibit SRS:

sodium 3,5-dimethylphenyl 3,5-dihydroxy-4-(3-(4-hydroxyphenyl) propionyl)phenyl phosphate sodium 3,5-dimethylphenyl 4-(3-(2,4,6-trihydroxyphenyl)-3-oxopropyl)phenyl phosphate sodium 4-(3-(2-hydroxyphenyl)-3-oxopropyl)phenyl phenyl phosphate sodium 3,5-dimethylphenyl 3-(3-(2-hydroxyphenyl)-3-oxopropyl)phenyl phosphate sodium 3-(3-(3,5-dimethyl-4-methoxyphenyl)-3-oxopropyl)phenyl phenyl phosphate sodium 4-fluorophenyl 4-(2,3-diphenyl)acryloyl)-3-methoxyphenyl phosphate sodium 4-(2-oxo-2-(2,4,6-trihydroxyphenyl)ethyl)phenyl phenyl phosphate sodium 3-hydroxy-4-benzoylphenyl phenyl phosphate sodium 4-(3,5-dimethylbenzoyl)phenyl phenyl phosphate sodium 4-(2(4-acetoxyphenyl)butyryl)phenyl phosphate From this example it is obvious that the new compounds also are useful as antagonists of SRS, a compound chemically related to the prostaglandins and known to be one of the substances which provokes bronchial asthma (for references see Brocklehurst, W.E., Progr. Allergy 6(1962) 539).

EXAMPLE 26

The effects of esters of the present invention on the anaphylactic reaction in guinea-pigs have been investigated using the isolated perfused guinea-pig lung preparation as described by Bhattacharya & Delaunois (Arch. Int. Pharmacodyn. 101:495, 1955). Guinea-pigs weighing about 300 g are sensitized with egg albumin according to Fredholm & Strandberg (1969). After the appropriate sensitization period the lungs are removed and mounted in a moist, thermostated chamber. The trachea and A. pulmonalis are cannulated. The arterial cannula is connected to a perfusion fluid reservoir containing Tyrode solution buffered with 10% Sorensen phosphate buffer. The tracheal cannula is connected with tubing to a carbogen gas supply delivering a constant amount per time unit. The perfusion pressure is measured in a side arm of the tubing with a "Mercury" transducer connected to an Ultralette UV-recorder. When antigen (egg albumin), 0.1 - 1.0 μg, is injected via the arterial cannula, a bronchoconstriction, indicated by an increase in the perfusion pressure, is elicited. When sodium 3,5-dimethylphenyl 4-(3-(2,4,6-trihydroxyphenyl)-3-oxopropyl)phenyl phosphate, 4–20 μg/ml, is incorporated in the Tyrode solution this anaphylactic bronchoconstriction is abolished or markedly reduced. The sodium salt of diphenyl phosphate completely lacked such an effect even when tested in the concentration 100 μg/ml.

Similar effects in a dose of about 0.5 - 2.0 mg are also obtained with the following compounds:

sodium 3,5-dihydroxy-4-(3-(4-hydroxyphenyl)acryloyl)phenyl phenyl phosphate sodium 3-(3-(2,4-dihydroxyphenyl)-3-oxopropyl)phenyl phenyl phosphate sodium 3-(3-(3,5-dimethyl-4-methoxyphenyl)-3-oxopropyl)phenyl phenyl phosphate sodium 4-(3-(4-diethylaminoethylphenyl)propionyl)phenyl phenyl phosphate sodium 1-hexyl 4-(3-oxo-3-phenylpropyl)phenyl phosphate sodium 4-(2-oxo-2-(2,4,6-trihydroxyphenyl)ethyl)phenyl phenyl phosphate sodium 3-hydroxy-4-benzoylphenyl phenyl phosphate sodium 4-(2-(4-hydroxyphenyl)butyryl)phenyl phenyl phosphate This example shows that the new compounds have utility in preventing an anaphylactic reaction.

EXAMPLE 27

Prepubertal rat ovaries are incubated with luteinizing hormone (LH) essentially according to Perklev and Ahren (Life Sciences Part I 10 (1971) 1387), one modification being the inclusion of theophylline into the Krebs-Ringer medium in order to inhibit the breakdown of cyclic AMP. After incubation, the ovaries are homogenized in trichloroacetic acid and cyclic AMP is determined in this extract after removal of the acid. Cyclic AMP is also determined in the incubation medium.

The method for the assay is modelled after that of Gilman (PROC. NATL. ACAD. SCI. U.S. 67 (1970) 305). The extract or the medium containing cyclic AMP is incubated with a protein kinase (prepared from rabbit skeletal muscle) in the presence of a known amount of tritium labelled cyclic AMP. The amount of labelled cyclic AMP bound to the protein kinase is proportional to the amount unlabelled cyclic AMP to be assayed, and is determined by liquid scintillation counting after isolating the kinasecyclic AMP complex by Millipore filtration.

When incubation of the prepubertal ovaries was carried out in the presence of sodium 3,5-dimethylphenyl 4-(3-(2,4,6-trihydroxyphenyl)-3-oxopropyl)phenyl phosphate the $ID_{50}$ (concentration of inhibitor resulting in 50% inhibition of the formation of cyclic AMP in the ovary as well as in the incubation medium) was $1.5 \times 10^{-5}$ M.

The following phosphoric acid esters have also been found to exert an inhibiting activity of the same order, when tested in the same in vitro system:
sodium 3,5-dimethylphenyl 3,5-dihydroxy-4-(3-(4-hydroxyphenyl) propionyl)phenyl phosphate
sodium 3-(3-(2,4-dihydroxyphenyl)-3-oxopropyl)phenyl phenyl phosphate
sodium 3-(3-(3,5-dimethyl-4-methoxyphenyl)-3-oxopropyl)phenyl phenyl phosphate
sodium 4-(3-(4-diethylaminophenyl)propionyl)phenyl phenyl phosphate
sodium 1-hexyl 4-(3-oxo-3-phenylpropyl)phenyl phosphate
sodium 4-(2-oxo-2-(2,4,6-trihydroxyphenyl)ethyl)phenyl phenyl phosphate
sodium 3-hydroxy-4-benzoylphenyl phenyl phosphate
sodium 4-(2-(4-hydroxyphenyl)butyryl)phenyl phenyl phosphate
sodium 4-(2-methoxycarbonyl benzoyl)phenyl phenyl phosphate From this example it is obvious that the new compounds are useful as inhibitors of the formation of cyclic-AMP and therefore will improve pathological conditions caused by an excessive formation of this compound.

EXAMPLE 28

This example illustrates the smooth muscle stimulatory effect of esters of this invention on the gerbil colon in vivo.

The experiments are performed with mongolian gerbils, anesthetized with pentobarbital, 50 mg/kg. The ascending colon is exposed and carefully stretched between silk thread loops and a strain-gauge transducer.

After a stable base-line has been established an ester of this invention, sodium 3,5-dimethylphenyl 4-(3-(2,4,6-trihydroxyphenyl)-3-oxopropyl)phenyl phosphate (Leo 1258) is infused i.v.

In doses from 40 mg/kg this treatment causes the gut to respond with a series of contractions. Sodium diphenyl phosphate causes no effect at all in doses up to 400 mg/kg.

When Leo 1258, in the concentration of 1 mg/ml, is incorporated in the buffer solution superfusing the gut, this reacts with an increase in tone, i.e. a contraction.

Similar effects are also obtained with the following compounds:
sodium 3,5-dihydroxy-4-(3-(4-hydroxyphenyl)acryloyl)phenyl phenyl phosphate
sodium 3-aminophenyl 4-(3-oxo-3-phenylpropyl)phenyl phosphate
sodium 1-hexyl 4-(3-oxo-3-phenylpropyl)phenyl phosphate
sodium 4-(3-(4-hydroxyphenyl)-3-oxopropyl)phenyl phenyl phosphate
sodium 4-(2-oxo-2-(2,4,6-trihydroxyphenyl)ethyl)phenyl phenyl phosphate
sodium 4-(2-carboxybenzoyl)phenyl phenyl phosphate
disodium salt of 4-(2-(4-dihydroxyphosphinyloxyphenyl)-1-oxo-3-phenyl-2-propenyl)phenyl phenyl hydrogen phosphate This example shows the usefulness of the new compounds in stimulation of smooth muscles.

EXAMPLE 29

The effects of esters of the present invention on bronchial smooth muscle have been investigated using an isolated perfused guinea-pig lung preparation according to Thattacharya & Delaunois (Arch. Int. Pharmacodyn. 101o:495, 1955). The lungs from guinea-pigs weighing 300–400 g are removed, and the trachea and A. pulmonalis cannulated. The arterial cannula is connected to a perfusion fluid reservoir containing Tyrode solution buffered with 10% Sorensen phosphate buffer. The tracheal cannula is connected with tubing to a carbogen gas supply delivering a constant amount per time unit. The perfusion pressure is measured in a side arm of the tubing with a "Mercury" transducer connected to an ultralette UV-recorder. The compounds are injected via the arterial cannula, close to the entrance of A. pulmonalis in the lung. In this type of experiments sodium 3,5-dimethylphenyl 4-(3-(2,4,6-trihydroxyphenyl)-3-oxo-propyl)phenyl phosphate showed a broncho-constricting effect, when administered in a dose of about 0.5 mg and upwards. The sodium salt of diphenyl phosphate completely lacked such an effect even when tested in the dose of 12.8 mg.

Similar effects in a dose of about 0.5 – 2.0 mg are also obtained with the following compounds.
sodium 3,5-dimethylphenyl 3,5-dihydroxy-4-(3-(4-hydroxyphenyl) propionyl)phenyl phosphate
sodium 4-(3-(4-diethylaminophenyl)propionyl)phenyl phenyl phosphate
sodium 4-(3-(4-carboxyphenyl)-2-(4-methoxyphenyl)acryloyl)-3-methoxyphenyl phenyl phosphate
sodium 4-(2-oxo-2-(2,4,6-trihydroxyphenyl)ethyl)pheny phenyl phosphate
sodium 2-naphthyl 4-(3-oxo-3-phenylpropyl)phenyl phosphate
sodium 4-(2-(4-hydroxyphenyl)butyryl)phenyl phenyl phosphate
sodium 2-(2,4-dimethylbenzoyl)phenyl phenyl phosphate This example shows the usefulness of the new compounds in stimulation of smooth muscles.

EXAMPLE 30

Effects of esters of the present invention are also studied on a rat uterus preparation, using an established technique (Staff of the Departing of Pharmacology, University of Edinburgh: Pharmacological Experiments on Isolated Preparations, E & S Livingstone Ltd, Edinburgh and London 1968). In the experiments uterine horns from diethylstilbestrol-treseted rats are suspended in a 6 ml bath containing modified de Jalon solution, kept at 28° C and gassed with air. When sodium 4-(3-oxo-3-(2,4,6-trihydroxyphenyl)propyl)phenyl phenyl phosphate is added in the concentration range 2–10 μg/ml a contraction is obtained demonstrating the smooth muscle stimulating action of this compound.

Similar effects are also obtained with the following compounds:

sodium 3,5-dimethylphenyl 3,5-dihydroxy-4-(3-(4-hydroxyphenyl) propionyl)phenyl phosphate sodium phenyl 4-(3-oxo-3-(2,4,6-trimethoxyphenyl)-propyl)phenyl phosphate sodium 3-hydroxy-4-(4-phenylbutyryl)phenyl 3,5-dimethoxyphenyl phosphate sodium 1-naphthyl 4-(3-oxo-3-phenylpropyl)phenyl phosphate sodium 4-(2-oxo-2-(2,4,6-trihydroxyphenyl)ethyl)phenyl phenyl phosphate sodium 3-hydroxy-4-benzoylphenyl phenyl phosphate This example shows the usefulness of the new compounds in stimulation of smooth muscles.

Example 31

Manufacturing Process for tablets at 25 mg. Model batch of 1000 tablets.

| | | | |
|---|---|---|---|
| I | Sodium 3,5-dimethylphenyl 4-(3-(2,4,6-triacetoxyphenyl)-3-oxopropyl)phenyl phosphate mesh 70 | 25.0 | g |
| | Lactosum, Ph.Nord. | 210 | g |
| | Amylum maidis, Ph.Nord. | 75 | g |
| II | Kollidon 25, B.A.S.F. | 3.5 | g |
| | Aqua purificata q.s. | | |
| III | Talcum, Ph.Nord. | 15 | g |
| | Magnesii stearas, Ph.Nord. | 1.5 | g |
| | Weight of 1000 tablets: | 330 | g |

Weight of 1 tablet: 330 mg

Punch: 10.5 mm round, flat, scored, bevel-edged.

Mix the screened substances I thoroughly and then moisten with II, whereupon it is granulated through a stainless sieve no. 10 (mesh 25). Dry the granulate in an oven at a maximum temperature of 40° C, then repeat sieving through sieve no. 10. Add the substances under III and mix thoroughly. Punch tablets with a gross weight of about 330 mg.

Example 32

Manufacturing Process for tablets at 25 mg. Model batch of 1000 tablets.

| | | | |
|---|---|---|---|
| I | Sodium 3,5-dimethylphenyl 4-(3-(2,4,6-trihydroxyphenyl)-3-oxopropyl)phenyl phosphate mesh 70 | 25.0 | g |
| II | Avicel, FMC Corporation, USA | 76 | g |
| | Amylum maidis, Ph.Nord. | 76 | g |
| | Calcii phosphas, Ph.Nord. | 76 | g |
| III | Talcum, Ph.Nord. | 15 | g |
| | Magnesii stearas, Ph.Nord. | 2 | g |
| | Weight of 1000 tablets | 270 | g |

Weight of 1 tablet: 270 mg

Punch: 9.0 mm round, normal concave.

Mix I by gradual stages with II. Add the substances under III and mix thoroughly. Punch tablets with a gross weight of about 270 mg.

Example 33

Oral suspension 5 mg/ml.

| | |
|---|---|
| Sodium phenyl 4-(3-oxo-3-(2,4,6-trimethoxyphenyl)propyl)phenyl phosphate | 5 mg |
| Sorbitol | 600 mg |
| Ascorbic acid | 100 mg |
| Flavouring compound | q.s. |
| Colour | q.s. |
| Water to make | 1 ml |

Example 34

Vagitoria 25 mg.

| | |
|---|---|
| Sodium 4-(2-(2,4,6-trimethoxyphenyl)-2-oxoethyl)phenyl 3,5-dimethylphenyl phosphate | 25 mg |
| Cacao butter | q.s. |

Example 35

Ointment 2 %

| | | |
|---|---|---|
| Sodium ethyl 4-(3-oxo-3-(2,4,6-triacetoxyphenyl)propyl)phenyl phopshate | 2 | g |
| Triethanolamine | 1 | g |
| Glycerol | 7 | g |
| Cetanol | 2.5 | g |
| Lanoline | 2.5 | g |
| Stearic acid | 20 | g |
| Sorbitan monooleate | 0.5 | g |
| Sodium hydroxide | 0.2 | g |
| Methyl paraben | 0.3 | g |
| Propyl paraben | 0.1 | g |
| Ethanol | 0.9 | g |
| Water to make | 100 | g |

Example 36

Eye-drops 2 %

| | |
|---|---|
| Sodium 4-(3-(4-hydroxyphenyl)-3-oxopropyl)phenyl phenyl phosphate | 20 mg |
| Boric acid | 10 mg |
| Cetylpyridinium chloride | 25 μg |
| Distilled water to make | 1 ml |

Example 37

Aerosol for inhalation

| | |
|---|---|
| Sodium 3,5-dimethylphenyl 4-(3-(2,4,6-trihydroxyphenyl)-3-oxopropyl)phenyl phosphate | 1 % |
| Isopropyl myristate | 1 % |
| Dichlorodifluoromethane | 39 % |
| Dichlorotetrafluoroethane | 59 % |

Filled in a container with metered valve.
Each dose gives

Example 38

Suspension for injection 20 mg/ml.

| | |
|---|---|
| Sodium phenyl 4-(3-oxo-3-(2,4,6-trimethoxyphenyl)propyl)phenyl phosphate | 20 mg |
| Sodium chloride | 8 mg |
| Carboxy methylcellulose | 1 mg |
| Benzyl alcohol | 1 mg |
| Distilled water to make | 1 ml |

Example 39

Injectable solution 20 mg/ml.

| | |
|---|---|
| Sodium 4-(3-(2,4-dihydroxyphenyl)-3-oxopropyl)phenyl 3,5-dimethyl phenyl phosphate | 20 mg |
| Ascorbic acid | 1 mg |
| Sodium bisulfite | 1 mg |
| Sodium chloride | 6 mg |
| Methyl paraben | 0.7 mg |
| Propyl paraben | 0.3 mg |
| Distilled water to make | 1 ml |

Example 40

Injectable solution 25 mg/ml.

| | |
|---|---|
| Sodium 4-(2,4,6-trimethoxybenzoyl)phenyl phenyl phosphate | 25 mg |
| Benzyl alcohol | 50 mg |

-continued

| Example 40 | |
|---|---|
| Injectable solution 25 mg/ml. | |
| Peanut oil to make | 1 ml |

| Example 41 | | |
|---|---|---|
| 40 mg Sterile powder to be dissolved in water for injection. | | |
| Sodium 3,5-dimethylphenyl 4-(3-(2,4,6-trihydroxyphenyl)-3-oxopropyl)-phenyl phosphate | 40 | mg |
| Sodium chloride | 4 | mg |
| Methyl paraben | 0.7 | mg |
| Propyl paraben | 0.3 | mg |
| The substances are dissolved in distilled water. The solution is dispensed in vials and freeze-dried. | | |

The above examples 31 – 41 to compositions are merely representative with regard to the active ingredients exemplified. It is to be understood that other compounds disclosed in the foregoing examples 1 – 18 may well be substituted for the active ingredients illustrated in the above examples.

also, it is to be noted that two or more compounds of the invention may be used in combination in the compositions illustrated, and also, if desired, in combination with other pharmacologically active agents.

Various modifications and equivalents will be apparent to one skilled in the art and may be made in the compounds, compositions and methods of the present invention without departing from the spirit or scope thereof, and it is therefore to be understood that the invention is not to be limited to the specific examples and embodiments disclosed herein.

We claim:

1. A novel secondary phosphoric acid ester compound having the general formula

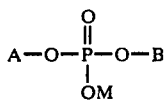
(I)

wherein M is selected from the group consisting of hydrogen; and a pharmaceutically acceptable inorganic and organic cations; and wherein A is

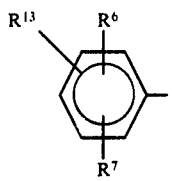

wherein one and only one of the substituents $R^6$, $R^7$, and $R^{13}$ always represents a group R, located in any of the ortho, meta and para positions relative to the phosphoric acid ester group, the group R having the formula

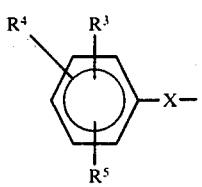

wherein X is selected from the group consisting of:

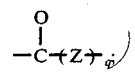

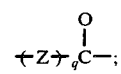

wherein $q$ is selected from the group consisting of zero and one; and wherein Z is selected from the group consisting of: straight saturated hydrocarbon chains having at most 3 carbon atoms; and straight hydrocarbon chains having 2 and 3 carbon atoms and containing one double bond; Z above may be substituted by one substituent selected from the group consisting of: lower alkyl; lower alkenyl; cyclopentyl; cyclohexyl; phenyl; phenyl substituted in m- or p-position by one substituent selected from the group consisting of lower alkyl, lower alkoxy, —F, —Cl, —Br, and —$CF_3$; benzyl; benzyl substituted in m- or p-position by one substituent selected from the group consisting of lower alkyl, lower alkoxy, —F, —Cl, —Br, and —$CF_3$; benzylidene; benzylidene substituted in m- or p-position by one substituent selected from the group consisting of lower alkyl, lower alkoxy, —F, —Cl, —Br, and —$CF_3$; wherein B in the general formula (I) above is selected from the group consisting of: alkyl; having one to eight carbon atoms, inclusive, being at most di-substituted; cycloalkyl, namely cyclopentyl and cyclohexyl, being at most di-substituted; 1- and 2-naphthyl, both naphthyls being at most di-substituted; 2-, 3- and 4-biphenylyl, any biphenylyl being at most di-substituted; and

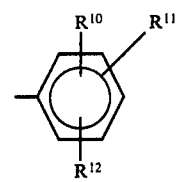

wherein the substituents in B, when B is alkyl, having one to eight carbon atoms, inclusive; cycloalkyl; naphthyl; or biphenylyl, are selected from the group consisting of lower alkyl, lower alkoxy, —F, —Cl, —Br, and —$CF_3$; wherein $R^3$, $R^4$, $R^5$, $R^6$, $R^7$, $R^{10}$, $R^{11}$, $R^{12}$, and $R^{13}$ above are selected from the group consisting of: hydrogen; lower alkyl; lower alkenyl; lower alkoxy; hydroxy; —O—CO—$R^{14}$; —F; —Cl; —Br; —$CF_3$; —CO—$R^{14}$; —$CONR_2^8$; —$CH_2CONR_2^8$; —$OCH_2$-$CONR_2^8$; —$NR^5$—CO—$R^{14}$; and —$CH_2NR^8$—CO—$R^{14}$; where $R^8$ is selected from the group consisting of hydrogen and lower alkyl; and where $R^{14}$ is lower alkyl, with the proviso that one of the substituents $R^3$, $R^4$, $R^5$, $R^6$, $R^7$, $R^{13}$ and one of the substituents $R^{10}$, $R^{11}$, and $R^{12}$ is selected from the group consisting of —$CONR_2^8$; —$CH_2CONR_2^8$; —$OCH_2CONR_2^8$; —$NR^8$—CO—$R^{14}$; and —$CH_2NR^8$—CO—$R^{14}$; $R^8$, and $R^{14}$ having the meaning given above; at least one of the substituents $R^3$, $R^4$, $R^5$, $R^6$, $R^7$, $R^{13}$, $R^{10}$, $R^{11}$, and $R^{12}$ being selected from the said latter group.

2. A method of treating a living animal body suffering from the actions of an excessive formation and release of endogenous prostaglandin or exposure to exogenous prostaglandin, comprising administration of a therapeutically-effective amount of a compound of claim 1 to said animal body.

3. A composition of matter comprising as an active ingredient a compound according to claim 1 in combination with a pharmaceutically acceptable carrier.

4. A compound according to claim 1, wherein at least one of the substituents $R^3$, $R^4$, $R^5$, $R^6$, $R^7$, and $R^{13}$ are hydrogen and wherein at least one of the substituents $R^{10}$, $R^{11}$ and $R^{12}$ also is hydrogen.

5. A compound according to claim 4, wherein the substituent R, having the meaning given in claim 1, is located in one of the m- and p-positions relative to the secondary phosphoric acid ester group.

6. A compound according to claim 5, wherein $q$ is selected from the group consisting of zero and one; and wherein Z is selected from the group consisting of straight hydrocarbon chains; and straight hydrocarbon chains substituted with a substituent selected from the group consisting of lower alkyl, and lower alkenyl.

7. A compound according to claim 5, wherein $q$ is one and wherein Z is a straight hydrocarbon chain having at most two carbon atoms and being substituted with a substituent selected from the group consisting of phenyl; substituted phenyl; benzyl; substituted benzyl, benzylidene; and substituted benzylidene.

8. A compound according to claim 6, wherein B is

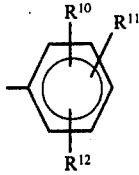

wherein $R^{10}$, $R^{11}$ and $R^{12}$ have the meaning given in claim 1.

9. A compound according to claim 6, wherein B is an alkyl group having at least four carbon atoms, and being at most di-substituted.

10. A compound according to claim 8, wherein at least two of the substituents $R^3$, $R^4$, $R^5$, $R^6$, $R^7$ and $R^{13}$, except the one being R, are selected from the group consisting of lower alkyl; lower alkoxy; hydroxy; and —O—CO—$R^{14}$; the remaining ones being hydrogen, and R and $R^{14}$ having the meaning given in claim 1.

11. A compound according to claim 8, wherein at least one of the substituents $R^3$, $R^4$, $R^5$, $R^6$, $R^7$, $R^{10}$, $R^{11}$, $R^{12}$ and $R^{13}$, except the one being R, are selected from the group consisting of —F; —Cl; —Br; and —$CF_3$, R having the meaning given in claim 1.

12. A compound according to claim 1 wherein M is selected from the group consisting of calcium; potassium; sodium; diethanolamine; dimethylaminoethanol; and N-methylglucamine.

13. A compound according to claim 8 selected from the group consisting of
sodium 4-(2-carbamoylbenzoyl)phenyl 3,5-dimethylphenyl phosphate
sodium 4-benzoyl-2,6-dimethylphenyl 3-acetylaminophenyl phosphate and
sodium 4-(3-(4-N,N,-dimethylcarbamoylmethylphenyl)-3-oxopropyl)phenyl 3,5-dimethylphenyl phosphate.

14. A compound according to claim 8 selected from the group consisting of
sodium 2-acetylaminomethyl-4-benzoyl-6-methylphenyl phenyl phosphate,
sodium 4-(3-acetylaminobenzoyl)phenyl 3,5-dimethylphenyl phosphate,
sodium 4-(3-(3-acetamidophenyl)-3-oxopropyl)phenyl phenyl phosphate, and
sodium 3-acetamidophenyl 4-(3-oxo-3-phenylpropyl)phenyl phosphate.

15. A compound according to claim 10 which is
sodium 3-(2,4,6-trimethylbenzoyl)phenyl 4-carbamoylphenyl phosphate.

16. A compound according to claim 8 selected from the group consisting of
sodium 4-benzoyl-3-carbamoylphenyl 3,5-dimethylphenyl phosphate,
sodium 4-benzoyl-3-carbamoylmethylphenyl 3,5-dimethylphenyl phosphate, and
sodium 4-benzoyl-3-carbamoylmethoxyphenyl 3,5-dimethylphenyl phosphate.

* * * * *

UNITED STATES PATENT OFFICE
CERTIFICATE OF CORRECTION

Patent No. 4,049,800  Dated Sept. 20, 1977

Inventor(s) Knut Bertil Hogberg et al.

It is certified that error appears in the above-identified patent and that said Letters Patent are hereby corrected as shown below:

Col. 1, line 29; "exort" should read --exert--
Col. 2, line 1; "primary⇌ " should read --primary--
Col. 3, line 32; "are" should read --as--
Col. 4, line 19; "seconary" should read --secondary--
Col. 4, line 43; "free or" should read --free of--
Col. 6, line 30; "cycloakyl" should read --cycloalkyl--
Col. 6, line 64; "have" should read --has--
Col. 7, line 30; "methylamine" should read -- -methylamine,--
Col. 7, line 68; "R3" should read --$R^3$--
Col. 8, line 42; "lowr" should read --lower--
Col. 14, line 52; "aerosls" should read --aerosols--
Col. 15, line 45; "coresponding" should read --corresponding--
Col. 17, line 61; "propiopenone" should read --propiophenone--
Col. 26, line 11; "cone." should read --conc.--
Col. 26, line 59; "firs" should read --first--
Col. 28, line 26; "solutin" should read --solution--
Col. 29, line 66; "2÷1" should read --2+1--
Col. 30, line 1; "meutralized" should read --neutralized--
Col. 32, line 23; "afteer" should read --after--

UNITED STATES PATENT OFFICE
CERTIFICATE OF CORRECTION

Patent No. 4,049,800  Dated Sept. 20, 1977

Inventor(s) Knut Bertil Hogberg et al.

It is certified that error appears in the above-identified patent and that said Letters Patent are hereby corrected as shown below:

Col. 33, line 66; "phoshate" should read --phosphate--
Col. 35, line 22; "tribenzoyloxy-acetophonone" should read --tribenzoyloxy-acetophenone--
Col. 35, line 51; "phophorur" should read --phosphorus--
Col. 35, line 56; "2,5" should read --2.5--
Col. 35, line 60; "wate" should read --water--
Col. 44, line 17; "1olo:495" should read --101:495--
Col. 44, line 26; "ultralette" should read --Ultralette--
Col. 48, line 1-10; "$-\overset{O}{\underset{|}{C}}(Z)_q$" should read --$-\overset{O}{\overset{\|}{C}}(Z)_q$--

"$(Z)_q \overset{O}{\underset{|}{C}}-$;" should read --$(Z)_q \overset{O}{\overset{\|}{C}}-$--

Col. 48, line 54; "$-NR^s-CO-R^{14}$" should read --$-NR^8-CO-R^{14}$--

Signed and Sealed this

Twenty-first Day of March 1978

[SEAL]

Attest:

RUTH C. MASON  
Attesting Officer

LUTRELLE F. PARKER  
Acting Commissioner of Patents and Trademarks